United States Patent
Moffitt et al.

(10) Patent No.: US 12,427,315 B2
(45) Date of Patent: *Sep. 30, 2025

(54) METHOD AND APPARATUS FOR SUBTRACTION-BASED PROGRAMMING OF NEUROSTIMULATION FIELDS

(71) Applicant: Boston Scientific Neuromodulation Corporation, Valencia, CA (US)

(72) Inventors: Michael A. Moffitt, Solon, OH (US); Rafael Carbunaru, Valley Village, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 106 days.

This patent is subject to a terminal disclaimer.

(21) Appl. No.: 18/195,853

(22) Filed: May 10, 2023

(65) Prior Publication Data

US 2023/0277849 A1    Sep. 7, 2023

Related U.S. Application Data

(63) Continuation of application No. 16/991,703, filed on Aug. 12, 2020, now Pat. No. 11,654,285.

(Continued)

(51) Int. Cl.
*A61N 1/36*  (2006.01)
*A61N 1/05*  (2006.01)

(52) U.S. Cl.
CPC ........ *A61N 1/36132* (2013.01); *A61N 1/0551* (2013.01); *A61N 1/0553* (2013.01); *A61N 1/0556* (2013.01)

(58) Field of Classification Search
CPC .................................................. A61N 1/36132
See application file for complete search history.

(56) References Cited

U.S. PATENT DOCUMENTS 9,067,076 B2    6/2015  Nolan et al.
11,654,285 B2 *  5/2023  Moffitt ............... A61N 1/36132
                                                607/59

(Continued)

OTHER PUBLICATIONS

"U.S. Appl. No. 16/991,703, Examiner Interview Summary mailed Oct. 26, 2022", 2 pgs.

(Continued)

*Primary Examiner* — Alyssa M Alter
(74) *Attorney, Agent, or Firm* — Schwegman Lundberg & Woessner, P.A.

(57) ABSTRACT

An example of a neurostimulation system may include a programming control circuit and a stimulation control circuit. The programming control circuit may be configured to program a stimulation device for delivering the neurostimulation according to a stimulation program specifying a present stimulation field set including stimulation field(s) each defined by a set of active electrodes selected from a plurality of electrodes. The stimulation control circuit may be configured to determine the stimulation program and may include field programming circuitry that may be configured to set the present stimulation field set to an initial stimulation field set specifying stimulation fields allowing for the delivery of the neurostimulation to produce an intended effect and to identify an optimal stimulation field set that satisfies one or more optimization criteria by removing stimulation field(s) from the initial stimulation field set.

20 Claims, 14 Drawing Sheets

Related U.S. Application Data

(60) Provisional application No. 62/887,290, filed on Aug. 15, 2019.

(56) References Cited

U.S. PATENT DOCUMENTS

| | | |
|---|---|---|
| 2004/0267330 A1 | 12/2004 | Lee et al. |
| 2017/0319860 A1 | 11/2017 | Goetz |
| 2021/0046316 A1 | 2/2021 | Moffitt et al. |

OTHER PUBLICATIONS

"U.S. Appl. No. 16/991,703, Non Final Office Action mailed Aug. 3, 2022", 11 pgs.
"U.S. Appl. No. 16/991,703, Notice of Allowance mailed Jan. 4, 2023", 8 pgs.
"U.S. Appl. No. 16/991,703, Response filed Oct. 27, 2022 to Non Final Office Action mailed Aug. 3, 2022", 14 pgs.

* cited by examiner

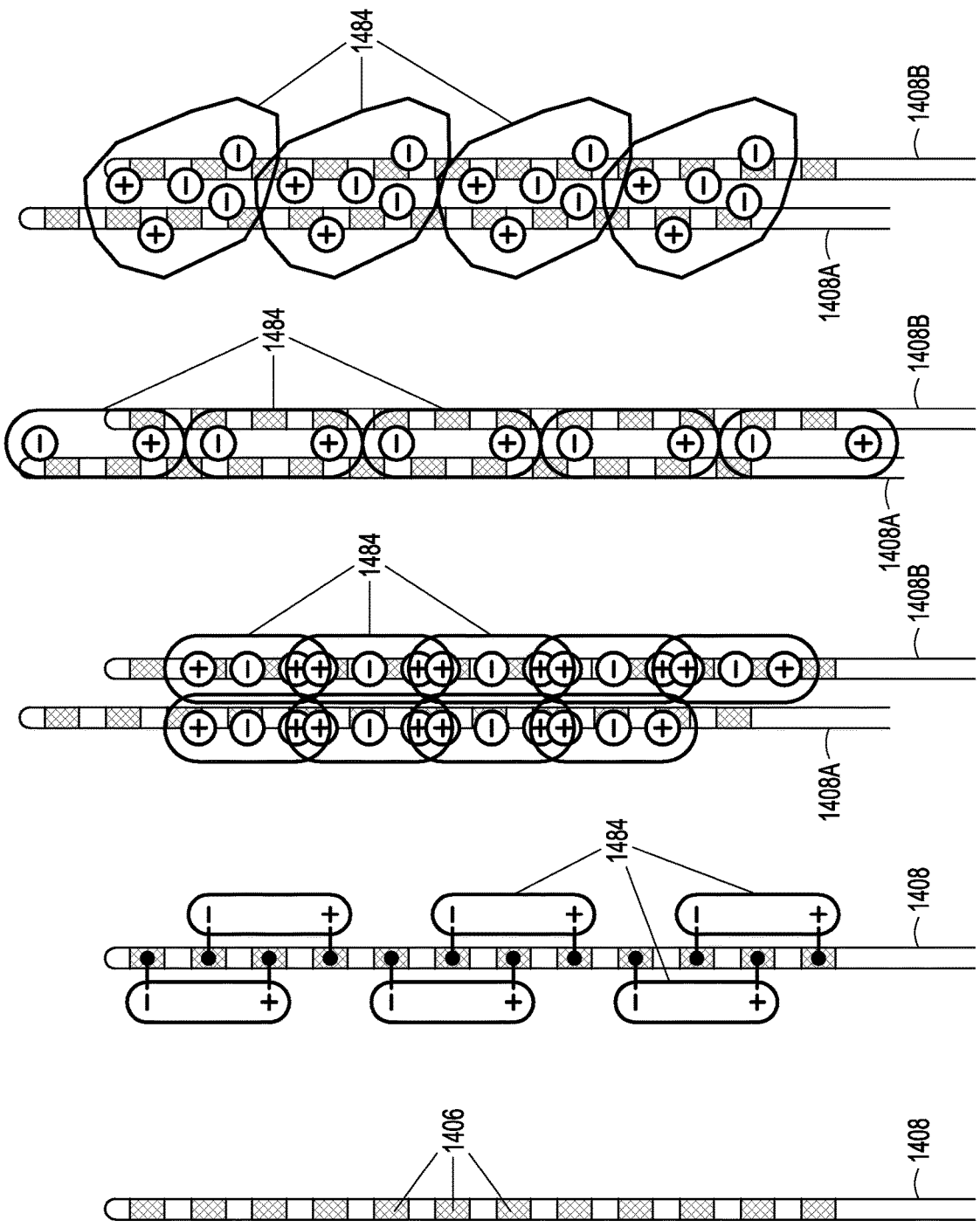

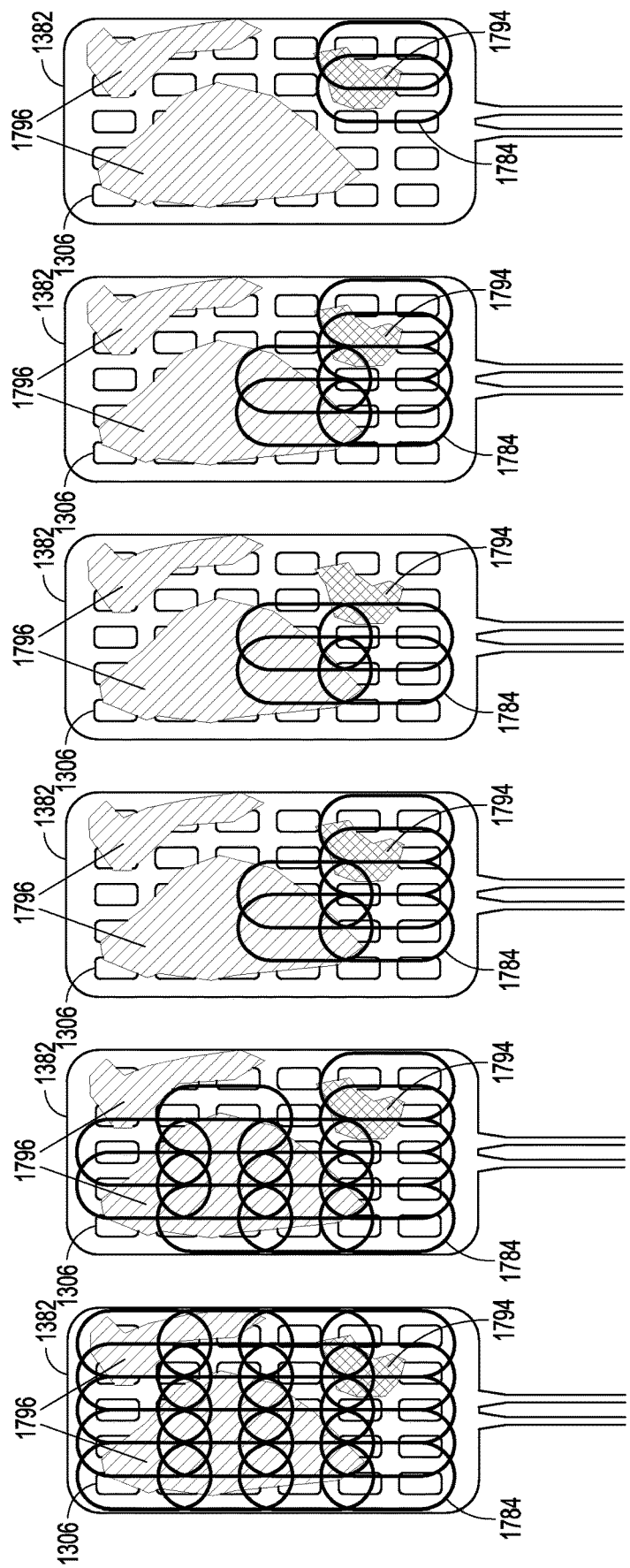

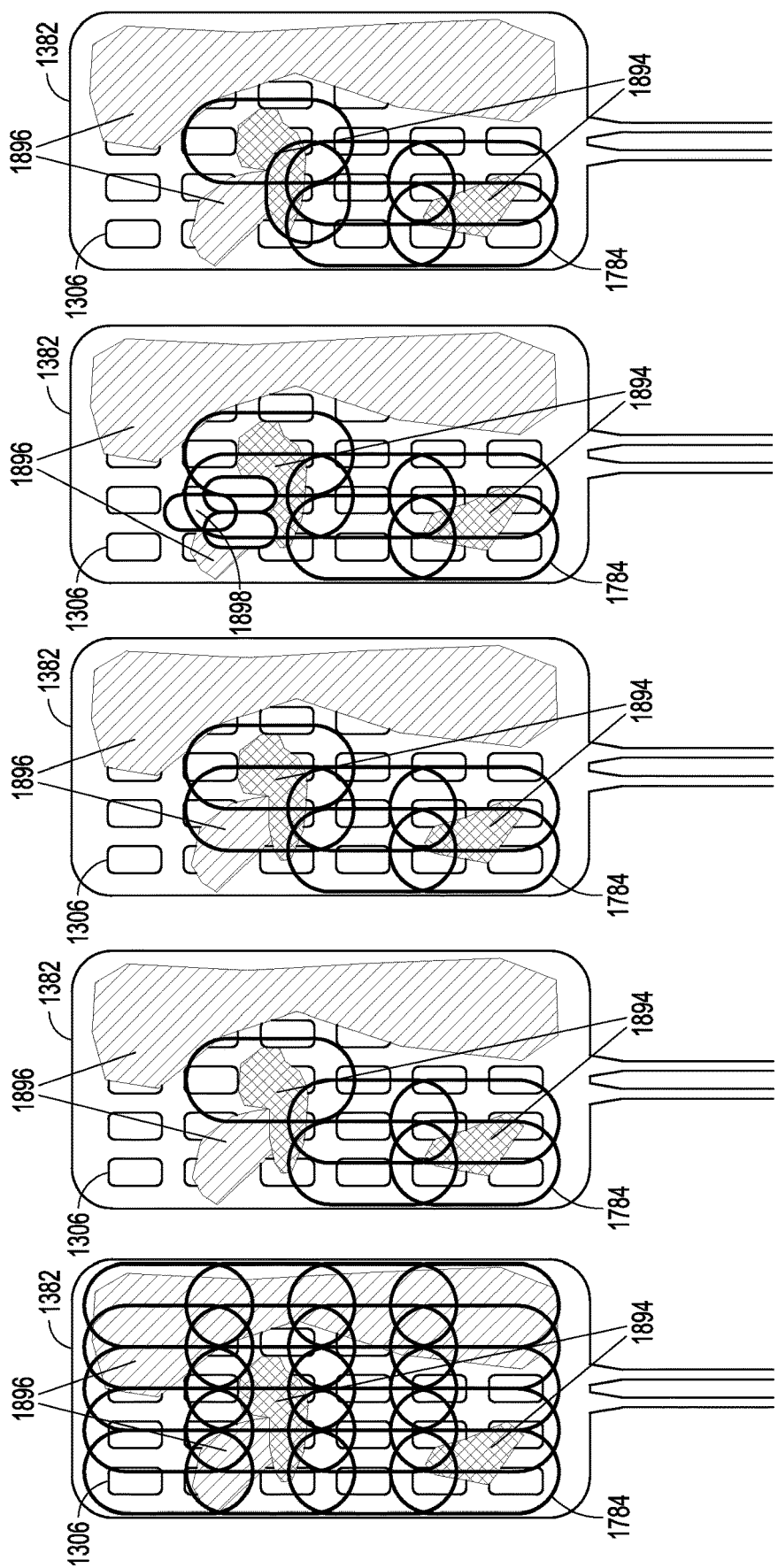

| TOOL | DESCRIPTION |
|---|---|
| ERASE TOOL | THE ERASE TOOL IS USED TO MANUALLY REMOVE FROM PARTS OF THE STIMULATION ARRAY (SIMILAR TO ERASING PIXELS IN MS PAINT, BUT REMOVING STIMULATION). COMPLEMENTARY TOOLS WOULD BE RESOLUTION (FOR REMOVING MORE OR LESS WITH A GIVEN CLICK), SHAPE (TO REMOVE WITH A SPECIFIC SHAPE), AND PRESS AND HOLD (ERASE WHILE MOVING THE TOOL). |
| ERASE SELECTION TOOL | THE ERASE SELECTION TOOL IS USED TO MANUALLY DRAW BORDERS WHICH ENCOMPASS AN AREA IN WHICH STIMULATION WILL BE REMOVED. THIS ENABLES REMOVAL OF BROAD SWATHS OF STIMULATION IN AREAS WHERE THERAPEUTIC STIM MAY NOT BE OCCURRING. SHOWN IS A RECTANGULAR TOOL, OF OTHER SHAPES COULD BE AVAILABLE FOR USE (E.G., CIRCLE, OVAL, RECTANGLE WITH ROUNDED EDGES, ETC.) |
| STIM SELECTION TOOL | THE STIM SELECTION TOOL IS SIMILAR TO THE ERASE SELECTION TOOL BUT WITH OPPOSITE BEHAVIOR; I.E., WITHIN THE SELECTED BORDERS, STIMULATION IS TURNED ON |
| BLOCK TOOL | THE BLOCK TOOL DEFINES AREAS THAT NOT ONLY ARE NOT STIMULATED (I.E., WITH INTENT TO ACTIVATE), BUT ARE MODULATED WITH INTENT TO PREVENT ACTIVATION USING FILED OR TIMING-BASED BLOCKING TECHNIQUES. (NOTE THAT THE BLOCK BEHAVIOR COULD ALSO BE COUPLED WITH A SELECTION TOOL TO CREATE A BLOCK SELECTION TOOL.) |
| UNDO (REDO) TOOL(S) | IN A REDUCTIONIST OR SUBTRACTION TYPE PROGRAMMING PARADIGM, IT IS USEFUL TO EASILY AND READILY UNDO YOUR ACTION (E.G., UNDO AN ERASE ACTION, BUT IT IS DETERMINED THAT AT LEAST PART OF THE STIMULATION THAT WAS ERASED IS EXPECTED TO BE CONTRIBUTING TO THERAPY). THE UNDO TOOL ENABLES A USER TO UNDO THE PREVIOUS ACTION, AND IDEALLY MULTIPLE ACTIONS WITH REPEATED PRESSES OF THE UNDO BUTTON. A REDO TOOL WITH OPPOSITE EFFECT WOULD ALSO BE USEFUL. |

FIG. 19

METHOD AND APPARATUS FOR SUBTRACTION-BASED PROGRAMMING OF NEUROSTIMULATION FIELDS

CLAIM OF PRIORITY

This application is a continuation of U.S. patent application Ser. No. 16/991,703, filed on Aug. 12, 2020, claims the benefit of priority under 35 U.S.C. § 119(e) of U.S. Provisional Patent Application Ser. No. 62/887,290, filed on Aug. 15, 2019, which are herein incorporated by reference in their entireties.

TECHNICAL FIELD

This document relates generally to medical devices and more particularly to a method and system for programming a neurostimulation device using a subtraction-based paradigm to determine stimulation fields.

BACKGROUND

Neurostimulation, also referred to as neuromodulation, has been proposed as a therapy for a number of conditions. Examples of neurostimulation include Spinal Cord Stimulation (SCS), Deep Brain Stimulation (DBS), Peripheral Nerve Stimulation (PNS), and Functional Electrical Stimulation (FES). Implantable neurostimulation systems have been applied to deliver such a therapy. An implantable neurostimulation system may include an implantable neurostimulator, also referred to as an implantable pulse generator (IPG), and one or more implantable leads each including one or more electrodes. The implantable neurostimulator delivers neurostimulation energy through one or more electrodes placed on or near a target site in the nervous system. An external programming device is used to program the implantable neurostimulator with stimulation parameters controlling the delivery of the neurostimulation energy.

In one example, the neurostimulation energy is delivered to a patient in the form of electrical neurostimulation pulses. The delivery is controlled using stimulation parameters that specify spatial (where to stimulate), temporal (when to stimulate), and informational (patterns of pulses directing the nervous system to respond as desired) aspects of a pattern of neurostimulation pulses. Stimulation parameters specifying the spatial aspects may determine where to place electrodes and/or which electrodes to select for delivering the neurostimulation pulses. This may include searching for locations in or on the patient that respond to the delivery of the neurostimulation pulses with desirable therapeutic effects as well as searching for locations in or on the patient that respond to the delivery of the neurostimulation pulses with undesirable side effects, such that the stimulation parameters can be determined for therapeutic effectiveness while ensuring patient safety and minimizing side effects.

SUMMARY

An example (e.g., "Example 1") of a system for delivering neurostimulation to tissue of a patient using a stimulation device coupled to a plurality of electrodes and controlling the delivery of the neurostimulation is provided. The system may include a programming control circuit and a stimulation control circuit. The programming control circuit may be configured to program the stimulation device for delivering the neurostimulation according to a stimulation program specifying a present stimulation field set including one or more stimulation fields each defined by a set of active electrodes selected from the plurality of electrodes. The stimulation control circuit may be configured to determine the stimulation program. The stimulation control circuit may include field programming circuitry that may be configured to set the present stimulation field set to an initial stimulation field set specifying a plurality of stimulation fields and allowing for the delivery of the neurostimulation to produce an intended effect in the patient and to identify an optimal stimulation field set that satisfies one or more optimization criteria by removing one or more stimulation fields from the initial stimulation field set, the optimal stimulation field set including one or more stimulation fields based on a subset of the plurality of stimulation fields of the initial stimulation field set.

In Example 2, the subject matter of Example 1 may optionally be configured such that the field programming circuitry is configured to further define the one or more stimulation fields by a distribution of energy of the neurostimulation over the active electrodes.

In Example 3, the subject matter of any one or any combination of Examples 1 and 2 may optionally be configured such that the field programming circuitry is configured to identify an optimal stimulation field set by removing at least one stimulation field from the present stimulation field set to update the present stimulation field set, causing the stimulation device to deliver the neurostimulation according to the stimulation program specifying the present stimulation field set, receiving a response signal indicative of effects of the neurostimulation delivered according to the stimulation program specifying the present stimulation field set, reverting the present stimulation field set to the pre-update present stimulation field set in response to the response signal indicating an unacceptable change to the effects indicated by the response signal, and repeating the removing, causing, receiving, and reverting until the present stimulation field set is determined to be the optimal stimulation field set according to the one or more optimization criteria.

In Example 4, the subject matter of Example 3 may optionally be configured to further include a user input device configured to receive a user input indicative of the patient's perception of the delivery of the neurostimulation, and such that the stimulation control circuit further includes a response input and response analysis circuitry. The response input is configured to receive a response signal indicative of effects of the neurostimulation, the response signal including the received user input. The response analysis circuitry is configured to analyze the received response signal and produce effects information allowing for the determination of whether the present stimulation field is the optimal stimulation field set according to the one or more optimization criteria.

In Example 5, the subject matter of any one or any combination of Examples 3 and 4 may optionally be configured such that the field programming circuitry is configured to revert the present stimulation field set to the pre-update present stimulation field set in response to the effects information indicating at least one of a decrease in the intended effect or an increase in an unintended effect.

In Example 6, the subject matter of Example 5 may optionally be configured such that the field programming circuitry is further configured to, after the reverting in response to the response signal indicating the increase in the unintended effect, add to the present stimulation field set one or more blocking fields to which the delivery of the neurostimulation has a blocking effect in preventing the delivery of the neurostimulation from causing the unintended effect or reducing the unintended effect.

In Example 7, the subject matter of Example 5 may optionally be configured such that the field programming circuitry is further configured to, after the reverting in response to the response signal indicating the increase in the unintended effect, modifying a shape of the present stimulation field set to prevent the delivery of the neurostimulation from causing the unintended effect or reduce the unintended effect.

In Example 8, the subject matter of any one or any combination of Examples 4 to 7 may optionally be configured such that the field programming circuitry is further configured to declare the present stimulation field set to be the optimal stimulation field set in response to the effects information indicating that the intended effect is maintained without causing an unintended effect.

In Example 9, the subject matter of any one or any combination of Examples 4 to 7 may optionally be configured such that the field programming circuitry is further configured to declare the present stimulation field set to be the optimal stimulation field set in response to the effects information indicating that the intended effect is maintained while one or more unintended effects are minimized.

In Example 10, the subject matter of any one or any combination of Examples 8 and 9 may optionally be configured such that the field programming circuitry is further configured to declare the present stimulation field set to be the optimal stimulation field set in response to the effects information indicating that the intended effect is maintained with energy of the delivered neurostimulation being minimized.

In Example 11, the subject matter of any one or any combination of Examples 4 to 7 may optionally be configured such that the field programming circuitry is further configured to identifying the optimal stimulation field set from a list of test stimulation field sets, and the repeating comprises repeating the removing, causing, receiving, and reverting until each test stimulation field set on the list is set to the present stimulation field set to result in the effects information allowing for the optimal stimulation field set to identified from the list for best satisfying the one or more optimization criteria.

In Example 12, the subject matter of any one or any combination of Examples 1 to 11 may optionally be configured to further include the stimulation device and a programmer configured to be communicatively coupled to the stimulation device. The programmer includes the programming control circuit and the stimulation control circuit.

In Example 13, the subject matter of Example 12 may optionally be configured such that the stimulation device comprises an implantable stimulation device, and the programmer comprises an external programmer.

An example (e.g., "Example 14") of a non-transitory computer-readable storage medium including instructions, which when executed by a machine, cause the machine to perform a method for delivering neurostimulation to tissue of a patient using a stimulation device coupled to a plurality of electrodes and controlling the delivery of the neurostimulation by a user is also provided. The method may include delivering the neurostimulation according to a stimulation program specifying a present stimulation field set including one or more stimulation fields each defined by a set of active electrodes selected from the plurality of electrodes, setting the present stimulation field set to an initial stimulation field set specifying a plurality of stimulation fields and allowing for the delivery of the neurostimulation to produce an intended effect in the patient, and identifying an optimal stimulation field set that satisfies one or more optimization criteria by removing one or more stimulation fields from the initial stimulation field set. The optimal stimulation field set may include one or more stimulation fields based on a subset of the plurality of stimulation fields of the initial stimulation field set.

In Example 15, the subject matter identifying the optimal stimulation field set as found in Example 14 may optionally be configured to include removing at least one stimulation field from the present stimulation field set to update the present stimulation field set, causing the stimulation device to deliver the neurostimulation according to the stimulation program specifying the present stimulation field set, receiving a response signal indicative of effects of the neurostimulation delivered according to the stimulation program specifying the present stimulation field set, reverting the present stimulation field set to the pre-update present stimulation field set in response to the response signal indicating an unacceptable change to the effects indicated by the response signal, and repeating the removing, causing, receiving, and reverting until the present stimulation field set is determined to be the optimal stimulation field set according to the one or more optimization criteria.

An example (e.g., "Example 16") of a method for delivering neurostimulation to tissue of a patient using a stimulation device coupled to a plurality of electrodes and controlling the delivery of the neurostimulation by a user is also provided. The method may include delivering the neurostimulation according to a stimulation program specifying a present stimulation field set including one or more stimulation fields each defined by a set of active electrodes selected from the plurality of electrodes, setting the present stimulation field set to an initial stimulation field set specifying a plurality of stimulation fields and allowing for the delivery of the neurostimulation to produce an intended effect in the patient, and identifying an optimal stimulation field set that satisfies one or more optimization criteria by removing one or more stimulation fields from the initial stimulation field set, the optimal stimulation field set including one or more stimulation fields based on a subset of the plurality of stimulation fields of the initial stimulation field set.

In Example 17, the subject matter of the one or more stimulation fields as found in Example 16 may optionally include the one or more stimulation fields each further defined by a distribution of energy of the neurostimulation over the active electrodes.

In Example 18, the subject matter of identifying the optimal stimulation field set as found in any one or any combination of Examples 16 and 17 may optionally include removing at least one stimulation field from the present stimulation field set to update the present stimulation field set, causing the stimulation device to deliver the neurostimulation according to the stimulation program specifying the present stimulation field set, receiving a response signal indicative of effects of the neurostimulation delivered according to the stimulation program specifying the present stimulation field set, reverting the present stimulation field set to the pre-update present stimulation field set in response to the response signal indicating an unacceptable change to the effects indicated by the response signal, and repeating the removing, causing, receiving, and reverting until the present stimulation field set is determined to be the optimal stimulation field set according to the one or more optimization criteria.

In Example 19, the subject matter of receiving the response signal as found in Example 18 may optionally include receiving a user input indicating the patient's perception of the delivery of the neurostimulation.

In Example 20, the subject matter of reverting the present stimulation field set to the pre-update present stimulation field set in response to the response signal indicating the unacceptable change to the effects indicated by the response signal as found in any one or any combination of Examples 18 and 19 may optionally include reverting the present stimulation field set to the pre-update present stimulation field set in response to the response signal indicating at least one of a decrease in the intended effect or an increase in an unintended effect.

In Example 21, the subject matter of Example 20 may optionally further include after the reverting in response to the response signal indicating the increase in the unintended effect, adding to the present stimulation field set one or more blocking fields to which the delivery of the neurostimulation has a blocking effect in preventing the delivery of the neurostimulation from causing the unintended effect or reducing the unintended effect.

In Example 22, the subject matter of Example 20 may optionally further include after the reverting in response to the response signal indicating the increase in the unintended effect, modifying a shape of the present stimulation field set to prevent the delivery of the neurostimulation from causing the unintended effect or reduce the unintended effect.

In Example 23, the subject matter of any one or any combination of Examples 18 to 22 may optionally include analyzing the received response signal to produce effects information allowing for determination of whether the present stimulation field set is the optimal stimulation field set based on the one or more optimization criteria.

In Example 24, the subject matter of the effects information as found in Example 23 may optionally include effects information indicating the unacceptable change to the effects of the neurostimulation delivered according to the stimulation program specifying the present stimulation field set.

In Example 25, the subject matter of Example 24 may optionally further include declaring the present stimulation field set to be the optimal stimulation field set in response to the effects information indicating that the intended effect is maintained without causing an unintended effect.

In Example 26, the subject matter of Example 25 may optionally further include declaring the present stimulation field set to be the optimal stimulation field set in response to the effects information indicating that the intended effect is maintained with energy of the delivered neurostimulation being minimized.

In Example 27, the subject matter of Example 24 may optionally further include declaring the present stimulation field set to be the optimal stimulation field set in response to the effects information indicating that the intended effect is maintained while one or more unintended effects are minimized.

In Example 28, the subject matter of identifying the optimal stimulation field set as found in any one or any combination of Examples 23 to 27 may optionally include identifying the optimal stimulation field set identified from a list of test stimulation field sets, and the subject matter of repeating as found in any one or any combination of Examples 23 to 27 may optionally include repeating the removing, causing, receiving, and reverting until each test stimulation field set on the list is set to the present stimulation field set to result in the effects information allowing for the optimal stimulation field set to identified from the list for best satisfying the one or more optimization criteria.

This Summary is an overview of some of the teachings of the present application and not intended to be an exclusive or exhaustive treatment of the present subject matter. Further details about the present subject matter are found in the detailed description and appended claims. Other aspects of the disclosure will be apparent to persons skilled in the art upon reading and understanding the following detailed description and viewing the drawings that form a part thereof, each of which are not to be taken in a limiting sense. The scope of the present disclosure is defined by the appended claims and their legal equivalents.

BRIEF DESCRIPTION OF THE DRAWINGS

The drawings illustrate generally, by way of example, various embodiments discussed in the present document. The drawings are for illustrative purposes only and may not be to scale.

FIGS. 14A-E each illustrate an embodiment of an electrode array at distal end of a lead to be percutaneously implanted for delivering neurostimulation, with FIGS. 14B-E each illustrating an example of a stimulation field set.

FIG. 17A-F each illustrate an embodiment of part of the method of FIG. 15 or 16.

FIG. 18A-E illustrates another embodiment of part of the method of FIG. 15 or 16.

FIG. 19 illustrates an embodiment of tools for editing a stimulation field set using a graphical user interface (GUI).

DETAILED DESCRIPTION

Figure 1:
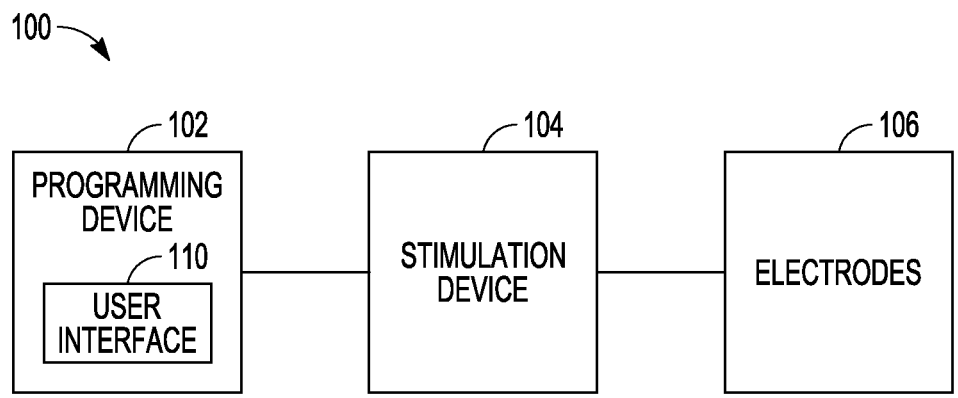
FIG. 1 illustrates an embodiment of a neurostimulation system.

In the following detailed description, reference is made to the accompanying drawings which form a part hereof, and in which is shown by way of illustration specific embodiments in which the invention may be practiced. These embodiments are described in sufficient detail to enable those skilled in the art to practice the invention, and it is to be understood that the embodiments may be combined, or that other embodiments may be utilized and that structural, logical and electrical changes may be made without departing from the spirit and scope of the present invention. References to "an", "one", or "various" embodiments in this disclosure are not necessarily to the same embodiment, and such references contemplate more than one embodiment. The following detailed description provides examples, and the scope of the present invention is defined by the appended claims and their legal equivalents.

This document discusses, among other things, a method and system for determining one or more stimulation fields for a neurostimulation system to deliver neurostimulation energy. In various embodiments, the neuromodulation system can include an implantable device configured to deliver neurostimulation (also referred to as neuromodulation) therapies, such as deep brain stimulation (DBS), spinal cord stimulation (SCS), peripheral nerve stimulation (PNS), and vagus nerve stimulation (VNS), and one or more external devices configured to program the implantable device for its operations and monitor the performance of the implantable device.

An effective neurostimulation therapy requires the neurostimulation energy to be delivered to a right location in or on the patient. When an implantable electrode array is used for delivering the neurostimulation energy, a stimulation field is to be programmed in a "right" location (known as a "sweet spot") by specifying one or more electrodes of the electrode array and/or a stimulation current distribution over electrodes of the electrode array. A sweet spot can be identified by testing one stimulation field at a time using a change-the-field (CTF) or move-the-field (MTF) paradigm. If one stimulation field does not provide an intended effect of neurostimulation, one or more stimulation fields are tested one at a time until the intended effect is obtained. This process can include testing multiple fields by any order of electrode configurations (CTF) or by modifying the electrode configuration in an incremental manner (MIT). A neurostimulation therapy program can include multiple fields in combination or one or more stimulation waveforms for desirable effects. Problems with the CTF and MTF paradigms include: (1) testing one stimulation field at time can be very time consuming; (2) in some cases (e.g., implantation of a lead) programming is required to know whether the electrode array is adequately positioned, but whether an adequate stimulation field can be identified using the positioned electrode array is not known until one is identified (after extensive searching sometimes); and (3) a stimulation program is often limited to one or two stimulation fields, though more stimulation fields may improve therapy efficacy, because each additional stimulation field may require significantly more time to identify (sweet spots need not be contiguous or near one another, but can be identified at different locations on the electrode array).

During the implantation of a lead including an electrode array, in an operation room, a goal is to place the electrode array in a location allowing neurostmulation to be delivered to result in a response that indicates potential therapeutic efficacy. In various embodiments, the responses can include perception of the neurostimulation by the patient, including but not limited to paresthesia. One or more stimulation fields can be identified, for example to maximize therapeutic effectiveness, minimize side effects, or optimize the therapy by reaching a desirable balance between therapeutic effectiveness and side effects. This identification or optimization process can be performed post-operationally to minimize the duration of the operation (e.g., the implantation of a neurostimulation system). In other words, the sweet spot(s) can be identified post-operationally while an adequate location for the electrode array is to be determined during the operation. This adequate location for the electrode array can be identified quickly by delivering the neurostimulation to many stimulation fields, for example in a sequential manner, without searching for the sweet spot(s) using a technique such as CTF or MTF.

The present subject matter provides for a subtraction-based or "reductionist" programming paradigm for identifying one or more optimal stimulation fields. A stimulation field is considered "optimal" or "optimized" for being the field identified from a group of test stimulation fields as the best to meet one or more specified criteria. The one or more specified criteria can include, but are not limited to, requirements for achieving certain therapy efficacy, avoiding or minimizing adverse side effects, providing for energy efficiency (e.g., when the therapy is delivered by a battery-powered system), and/or ensuring patient safety. The subtraction-based programming starts with testing many stimulation fields, for example in a sequential manner, to achieve therapy efficacy. A subtraction-based iterative process follows by removing (i.e., subtracting) a set of one or more stimulation fields and evaluating the response for the one or more specified criteria for each iteration, until the one or more optimal stimulation fields are identified.

In this document, unless noted otherwise, a "patient" includes a person who receives or is intended to receive treatment delivered from a neurostimulation system according to the present subject matter, and a "user" includes a clinician or other caregiver who sets up the neurostimulation system for and/or treats the patient using the neurostimulation system.

FIG. 1 illustrates an embodiment of a neurostimulation system 100. System 100 includes electrodes 106, a stimulation device 104, and a programming device 102. Electrodes 106 are configured to be placed on or near one or more neural targets in a patient. Stimulation device 104 is configured to be electrically connected to electrodes 106 and deliver neurostimulation energy, such as in the form of electrical pulses, to the one or more neural targets though electrodes 106. The delivery of the neurostimulation is controlled by using a plurality of stimulation parameters, such as stimulation parameters specifying a pattern of the electrical pulses and a selection of electrodes through which each of the electrical pulses is delivered. In various embodiments, at least some parameters of the plurality of stimulation parameters are programmable by the user. Programming device 102 provides the user with accessibility to the user-programmable parameters. In various embodiments, programming device 102 is configured to be communicatively coupled to stimulation device via a wired or wireless link. In various embodiments, the patient can be allowed to adjust his or her treatment using system 100 to certain extent, such as by adjusting certain therapy parameters and entering feedback and clinical effect information.

In various embodiments, programming device 102 can include a user interface 110 that allows the user to control the operation of system 100 and monitor the performance of system 100 as well as conditions of the patient including responses to the delivery of the neurostimulation. The user can control the operation of system 100 by setting and/or adjusting values of the user-programmable parameters.

In various embodiments, user interface 110 can include a graphical user interface (GUI) that allows the user to set and/or adjust the values of the user-programmable parameters by creating and/or editing graphical representations of various waveforms. Such waveforms may include, for example, a waveform representing a pattern of neurostimulation pulses to be delivered to the patient as well as individual waveforms that are used as building blocks of the pattern of neurostimulation pulses, such as the waveform of each pulse in the pattern of neurostimulation pulses. The GUI may also allow the user to set and/or adjust stimulation fields each defined by a set of electrodes through which one or more neurostimulation pulses represented by a waveform are delivered to the patient. The stimulation fields may each be further defined by the distribution of the current of each neurostimulation pulse in the waveform. In various embodiments, neurostimulation pulses for a stimulation period (such as the duration of a therapy session) may be delivered to multiple stimulation fields.

In various embodiments, system 100 can be configured for neurostimulation applications. User interface 110 can be configured to allow the user to control the operation of system 100 for neurostimulation. For example, system 100 as well as user interface 100 can be configured for SCS applications. While an SCS system is illustrated and discussed as an example, the present subject matter applies to any neurostimulation system with electrodes placed in locations suitable for sensing one or more neural signals from which indications of degenerative and/or other nerve diseases can be detected and monitored.

Figure 2:
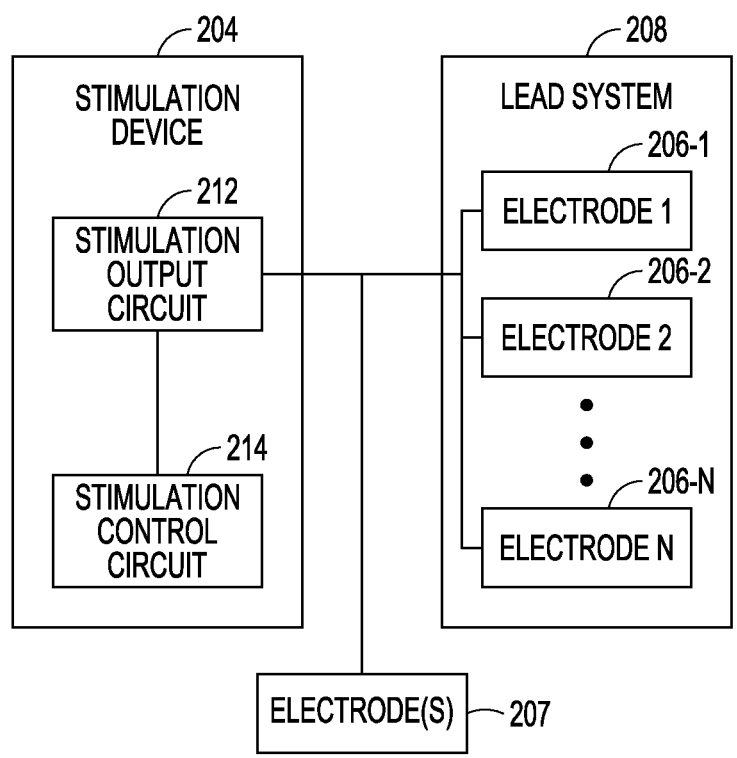
FIG. 2 illustrates an embodiment of a stimulation device and a lead system, such as may be implemented in the neurostimulation system of FIG. 1.

FIG. 2 illustrates an embodiment of a stimulation device 204 and a lead system 208, such as may be implemented in neurostimulation system 100. Stimulation device 204 represents an example of stimulation device 104 and includes a stimulation output circuit 212 and a stimulation control circuit 214. Stimulation output circuit 212 produces and delivers neurostimulation pulses. Stimulation control circuit 214 controls the delivery of the neurostimulation pulses from stimulation output circuit 212 using the plurality of stimulation parameters, which specifies a pattern of the neurostimulation pulses. Lead system 208 includes one or more leads each configured to be electrically connected to stimulation device 204 and a plurality of electrodes 206 distributed in the one or more leads. The plurality of electrodes 206 includes electrode 206-1, electrode 206-2, . . . electrode 206-N, each a single electrically conductive contact providing for an electrical interface between stimulation output circuit 212 and tissue of the patient, where N≥2. The neurostimulation pulses are each delivered from stimulation output circuit 212 through a set of electrodes selected from electrodes 206. In various embodiments, the neurostimulation pulses may include one or more individually defined pulses, and the set of electrodes may be individually definable by the user for each of the individually defined pulses or each of collections of pulses intended to be delivered using the same combination of electrodes. In various embodiments, one or more additional electrodes 207 (each of which may be referred to as a reference electrode) can be electrically connected to stimulation device 204, such as one or more electrodes each being a portion of or otherwise incorporated onto a housing of stimulation device 204. Monopolar stimulation uses a monopolar electrode configuration with one or more electrodes selected from electrodes 206 and at least one electrode from electrode(s) 207. Bipolar stimulation uses a bipolar electrode configuration with two electrodes selected from electrodes 206 and none electrode(s) 207. Multipolar stimulation uses a multipolar electrode configuration with multiple (two or more) electrodes selected from electrodes 206 and optionally electrode(s) 207.

In various embodiments, the number of leads and the number of electrodes on each lead depend on, for example, the distribution of target(s) of the neurostimulation and the need for controlling the distribution of electric field at each target. In one embodiment, lead system 208 includes 2 leads each having 8 electrodes. Lead and electrode configurations are illustrated in this document as examples and not limitations. For example, various embodiments can use paddle electrodes, cuff electrodes, and other electrodes suitable for delivering neurostimulation.

Figure 3:
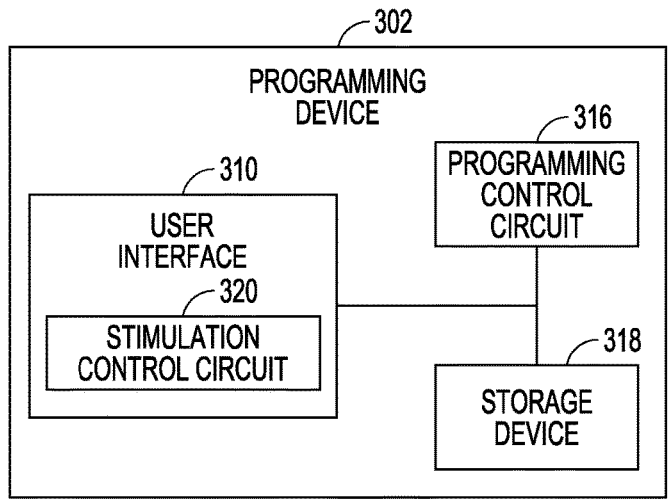
FIG. 3 illustrates an embodiment of a programming device, such as may be implemented in the neurostimulation system of FIG. 1.

FIG. 3 illustrates an embodiment of a programming device 302, such as may be implemented in neurostimulation system 100. Programming device 302 represents an example of programming device 102 and includes a storage device 318, a programming control circuit 316, and a user interface 310. Programming control circuit 316 generates the plurality of stimulation parameters that controls the delivery of the neurostimulation pulses according to a specified neurostimulation program that can define, for example, stimulation waveform and electrode configuration. User interface 310 represents an example of user interface 110 and includes a stimulation control circuit 320. Storage device 318 stores information used by programming control circuit 316 and stimulation control circuit 320, such as information about a stimulation device that relates the neurostimulation program to the plurality of stimulation parameters. In various embodiments, stimulation control circuit 320 can be configured to support one or more functions allowing for programming of stimulation devices, such as stimulation device 104 including its various embodiments as discussed in this document, according to one or more selected neurostimulation programs as discussed in this document.

In various embodiments, user interface 310 can allow for definition of a pattern of neurostimulation pulses for delivery during a neurostimulation therapy session by creating and/or adjusting one or more stimulation waveforms using a graphical method. The definition can also include definition of one or more stimulation fields each associated with one or more pulses in the pattern of neurostimulation pulses. As used in this document, a "neurostimulation program" can include the pattern of neurostimulation pulses including the one or more stimulation fields, or at least various aspects or parameters of the pattern of neurostimulation pulses including the one or more stimulation fields. In various embodiments, user interface 310 includes a GUI that allows the user to define the pattern of neurostimulation pulses and perform other functions using graphical methods. In this document, "neurostimulation programming" can include the definition of the one or more stimulation waveforms, including the definition of one or more stimulation fields.

In various embodiments, circuits of neurostimulation 100, including its various embodiments discussed in this document, may be implemented using a combination of hardware and software. For example, the circuit of user interface 110, stimulation control circuit 214, programming control circuit 316, and stimulation control circuit 320, including their various embodiments discussed in this document, may be implemented using an application-specific circuit constructed to perform one or more particular functions or a general-purpose circuit programmed to perform such function(s). Such a general-purpose circuit can include, but is not limited to, a microprocessor or a portion thereof, a microcontroller or portions thereof, and/or a programmable logic circuit or a portion thereof.

Figure 4:
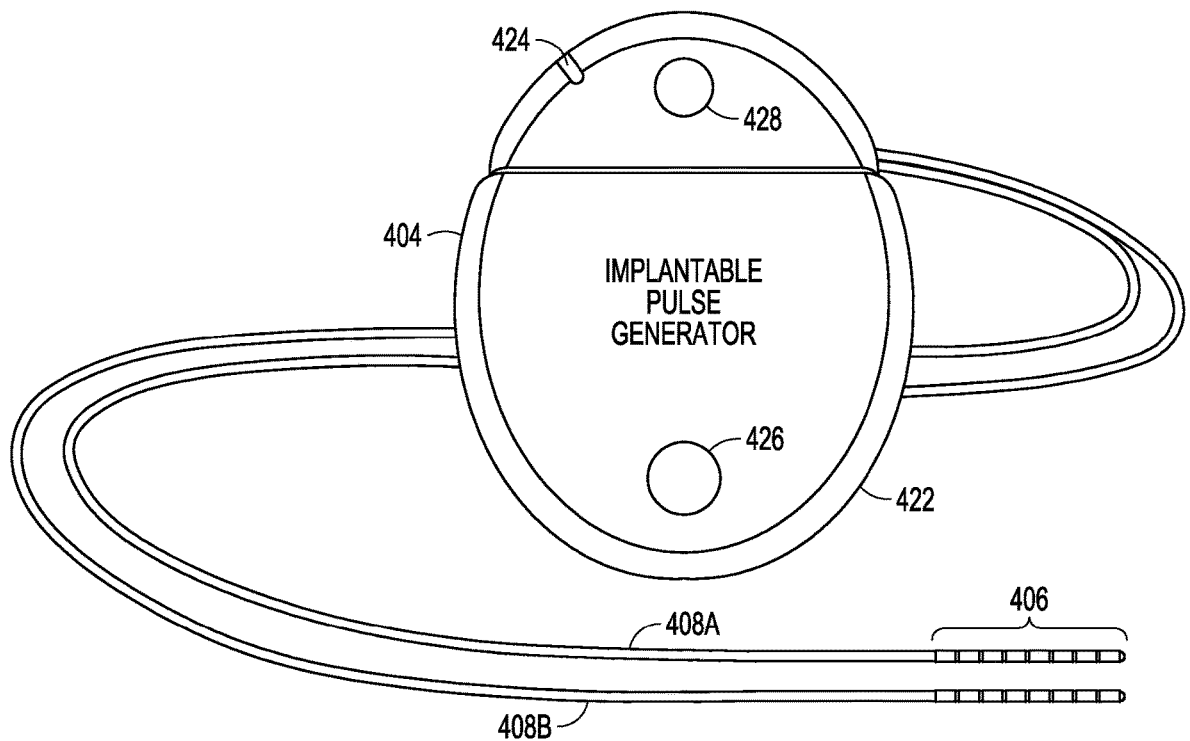
FIG. 4 illustrates an embodiment of an implantable pulse generator (IPG) and an implantable lead system, such as an example implementation of the stimulation device and lead system of FIG. 2.

FIG. 4 illustrates an embodiment of an implantable pulse generator (IPG) 404 and an implantable lead system 408. IPG 404 represents an example implementation of stimulation device 204. Lead system 408 represents an example implementation of lead system 208. As illustrated in FIG. 4, IPG 404 that can be coupled to implantable leads 408A and 408B at a proximal end of each lead. The distal end of each lead includes electrical contacts or electrodes 406 for contacting a tissue site targeted for electrical neurostimulation. As illustrated in FIG. 1, leads 408A and 408B each include 8 electrodes 406 at the distal end. The number and arrangement of leads 408A and 408B and electrodes 406 as shown in FIG. 1 are only an example, and other numbers and arrangements are possible. In various embodiments, the electrodes are ring electrodes. The implantable leads and electrodes may be configured by shape and size to provide electrical neurostimulation energy to a neuronal target included in the subject's brain or configured to provide electrical neurostimulation energy to target nerve cells in the subject's spinal cord.

Figure 5:
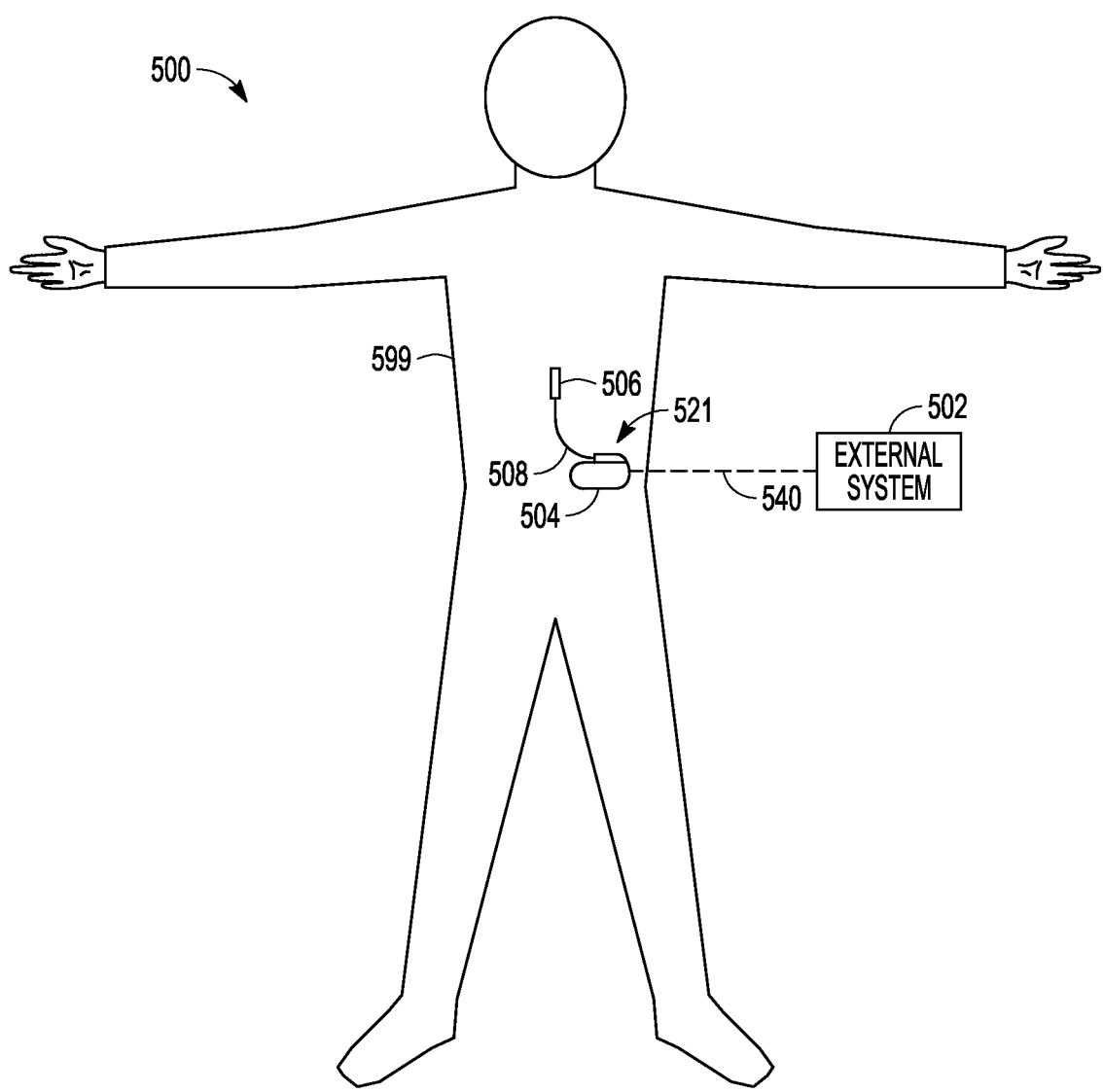
FIG. 5 illustrates an implantable neurostimulation system, such as an example application of the IPG and implantable lead system of FIG. 4, and portions of an environment in which the system may be used.

FIG. 5 illustrates an implantable neurostimulation system 500 and portions of an environment in which system 500 may be used. System 500 includes an implantable system 521, an external system 502, and a telemetry link 540 providing for wireless communication between implantable system 521 and external system 502. Implantable system 521 is illustrated in FIG. 5 as being implanted in the patient's body 599.

Implantable system 521 includes an implantable stimulator (also referred to as an implantable pulse generator, or IPG) 504, a lead system 508, and electrodes 506, which represent an example of stimulation device 204, lead system 208, and electrodes 206, respectively. External system 502 represents an example of programming device 302. In various embodiments, external system 502 includes one or more external (non-implantable) devices each allowing the user and/or the patient to communicate with implantable system 521. In some embodiments, external system 502 includes a programming device intended for the user to initialize and adjust settings for implantable stimulator 504 and a remote control device intended for use by the patient. For example, the remote control device may allow the patient to turn implantable stimulator 504 on and off and/or adjust certain patient-programmable parameters of the plurality of stimulation parameters.

The sizes and shapes of the elements of implantable system 521 and their location in body 599 are illustrated by way of example and not by way of restriction. An implantable system is discussed as a specific application of the programming according to various embodiments of the present subject matter. In various embodiments, the present subject matter may be applied in programming any type of stimulation device that uses electrical pulses as stimuli, regardless of stimulation targets in the patient's body and whether the stimulation device is implantable.

Returning to FIG. 4, the IPG 404 can include a hermetically-sealed IPG case 422 to house the electronic circuitry of IPG 404. IPG 404 can include an electrode 426 formed on IPG case 422. IPG 404 can include an IPG header 424 for coupling the proximal ends of leads 408A and 408B. IPG header 424 may optionally also include an electrode 428. Electrodes 426 and/or 428 represent embodiments of electrode(s) 207 and may each be referred to as a reference electrode. Neurostimulation energy can be delivered in a monopolar (also referred to as unipolar) mode using electrode 426 or electrode 428 and one or more electrodes selected from electrodes 406. Neurostimulation energy can be delivered in a bipolar mode using a pair of electrodes of the same lead (lead 408A or lead 408B). Neurostimulation energy can be delivered in an extended bipolar mode using one or more electrodes of a lead (e.g., one or more electrodes of lead 408A) and one or more electrodes of a different lead (e.g., one or more electrodes of lead 408B).

The electronic circuitry of IPG 404 can include a control circuit that controls delivery of the neurostimulation energy. The control circuit can include a microprocessor, a digital signal processor, application specific integrated circuit (ASIC), or other type of processor, interpreting or executing instructions included in software or firmware. The neurostimulation energy can be delivered according to specified (e.g., programmed) modulation parameters. Examples of setting modulation parameters can include, among other things, selecting the electrodes or electrode combinations used in the stimulation, configuring an electrode or electrodes as the anode or the cathode for the stimulation, specifying the percentage of the neurostimulation provided by an electrode or electrode combination, and specifying stimulation pulse parameters. Examples of pulse parameters include, among other things, the amplitude of a pulse (specified in current or voltage), pulse duration (e.g., in microseconds), pulse rate (e.g., in pulses per second), and parameters associated with a pulse train or pattern such as burst rate (e.g., an "on" modulation time followed by an "off" modulation time), amplitudes of pulses in the pulse train, polarity of the pulses, etc.

Figure 6:
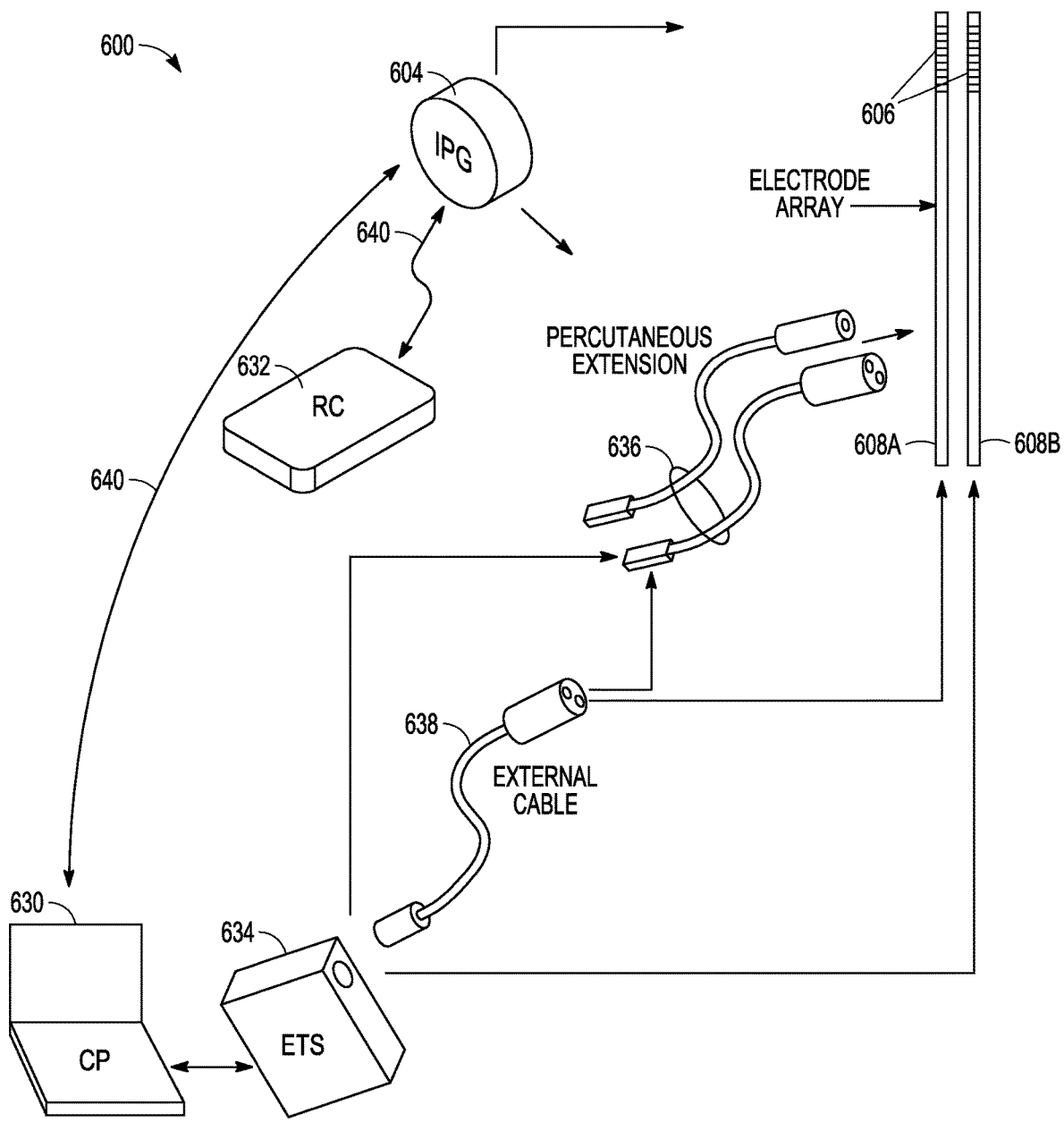
FIG. 6 illustrates an embodiment of portions of a neurostimulation system.

FIG. 6 illustrates an embodiment of portions of a neurostimulation system 600. System 600 includes an IPG 604, implantable neurostimulation leads 608A and 608B, an external remote controller (RC) 632, a clinician's programmer (CP) 630, and an external trial stimulator (ETS, also referred to as external trial modulator, or ETM) 634. IPG 404 may be electrically coupled to leads 608A and 608B directly or through percutaneous extension leads 636. ETS 634 may be electrically connectable to leads 608A and 608B via one or both of percutaneous extension leads 636 and/or external cable 638. System 600 represents an example of system 100, with IPG 604 representing an embodiment of stimulation device 104, electrodes 606 of leads 608A and 608B representing electrodes 106, and CP 630, RC 632, and ETS 634 collectively representing programming device 102.

ETS 634 may be standalone or incorporated into CP 630. ETS 634 may have similar pulse generation circuitry as IPG 604 to deliver neurostimulation energy according to specified modulation parameters as discussed above. ETS 634 is an external device configured for ambulatory use and may be used as a preliminary stimulator after leads 408A and 408B have been implanted and used prior to stimulation with IPG 604 to test the patient's responsiveness to the stimulation that is to be provided by IPG 604. ETS 634 may include cable connectors allowing it to readily interface the proximal end of external leads that are for chronic use, and may include replaceable batteries.

CP 630 can configure the neurostimulation provided by ETS 634. If ETS 634 is not integrated into CP 630, CP 630 may communicate with ETS 634 using a wired connection (e.g., over a USB link) or by wireless telemetry using a wireless communications link 640. CP 630 also communicates with TPG 604 using a wireless communications link 640.

An example of wireless telemetry is based on inductive coupling between two closely-placed coils using the mutual inductance between these coils. This type of telemetry is referred to as inductive telemetry or near-field telemetry because the coils must typically be closely situated for obtaining inductively coupled communication. IPG 604 can include the first coil and a communication circuit. CP 630 can include or be otherwise electrically connected to the second coil such as in the form of a wand that can be place near IPG 604. Another example of wireless telemetry includes a far-field telemetry link, also referred to as a radio frequency (RF) telemetry link. A far-field, also referred to as the Fraunhofer zone, refers to the zone in which a component of an electromagnetic field produced by the transmitting electromagnetic radiation source decays substantially proportionally to 1/r, where r is the distance between an observation point and the radiation source. Accordingly, far-field refers to the zone outside the boundary of $r=\lambda/2\pi$, where $\lambda$ is the wavelength of the transmitted electromagnetic energy. In one example, a communication range of an RF telemetry link is at least six feet but can be as long as allowed by the particular communication technology. RF antennas can be included, for example, in the header of IPG 604 and in the housing of CP 630, eliminating the need for a wand or other means of inductive coupling. An example is such an RF telemetry link is a Bluetooth® wireless link.

CP 630 can be used to set modulation parameters for the neurostimulation after IPG 604 has been implanted. This allows the neurostimulation to be tuned if the requirements for the neurostimulation change after implantation. CP 630 can also upload information from IPG 604.

RC 632 also communicates with IPG 604 using a wireless link 340. RC 632 may be a communication device used by the user or given to the patient. RC 632 may have reduced programming capability compared to CP 630. This allows the user or patient to alter the neurostimulation therapy but does not allow the patient full control over the therapy. For example, the patient may be able to increase the amplitude of neurostimulation pulses or change the time that a pre-programmed stimulation pulse train is applied. RC 632 may be programmed by CP 630. CP 630 may communicate with the RC 632 using a wired or wireless communications link. In some embodiments, CP 630 can program RC 632 when remotely located from RC 632.

Figure 7:
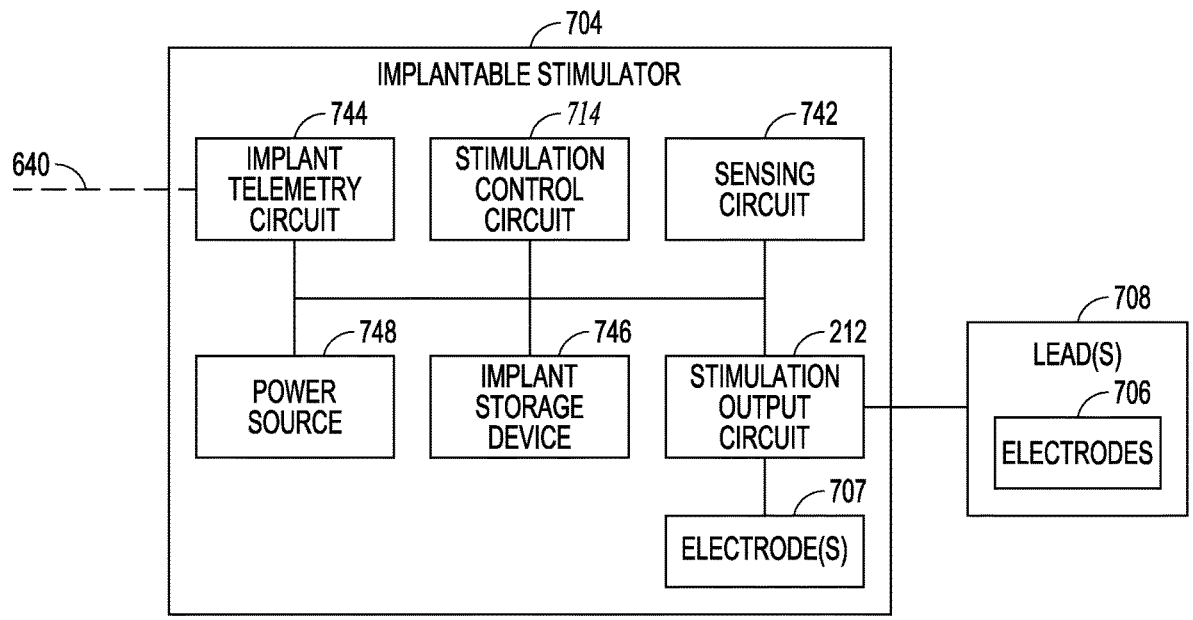
FIG. 7 illustrates an embodiment of an implantable stimulator and one or more leads of an implantable neurostimulation system, such as the implantable neurostimulation system of FIG. 6.

FIG. 7 illustrates an embodiment of implantable stimulator 704 and one or more leads 708 of an implantable neurostimulation system, such as implantable system 600. Implantable stimulator 704 represents an example of stimulation device 104 or 204 and may be implemented, for example, as IPG 604. Lead(s) 708 represents an example of lead system 208 and may be implemented, for example, as implantable leads 608A and 608B. Lead(s) 708 includes electrodes 706, which represents an example of electrodes 106 or 206 and may be implemented as electrodes 606.

Implantable stimulator 704 may include a sensing circuit 742 that is optional and required only when the stimulator needs a sensing capability, stimulation output circuit 212, a stimulation control circuit 714, an implant storage device 746, an implant telemetry circuit 744, a power source 748, and one or more electrodes 707. Sensing circuit 742 senses one or more physiological signals for purposes of patient monitoring and/or feedback control of the neurostimulation. Examples of the one or more physiological signals include neural and other signals each indicative of a condition of the patient that is treated by the neurostimulation and/or a response of the patient to the delivery of the neurostimulation. In various embodiments, sensing circuit 742 senses one or more neural signals and detects one or more indications of a neurodegenerative disease, as further discussed with reference to FIGS. 9-16. Stimulation output circuit 212 is electrically connected to electrodes 706 through one or more leads 708 as well as electrodes 707 and delivers each of the neurostimulation pulses through a set of electrodes selected from electrodes 706 and electrode(s) 707. Stimulation control circuit 714 represents an example of stimulation control circuit 214 and controls the delivery of the neurostimulation pulses using the plurality of stimulation parameters specifying the pattern of neurostimulation pulses. In one embodiment, stimulation control circuit 714 controls the delivery of the neurostimulation pulses using the one or more sensed physiological signals. Implant telemetry circuit 744 provides implantable stimulator 704 with wireless communication with another device such as CP 630 and RC 632, including receiving values of the plurality of stimulation parameters from the other device. Implant storage device 746 can store one or more neurostimulation programs and values of the plurality of stimulation parameters for each of the one or more neurostimulation programs. Power source 748 provides implantable stimulator 704 with energy for its operation. In one embodiment, power source 748 includes a battery. In one embodiment, power source 748 includes a rechargeable battery and a battery charging circuit for charging the rechargeable battery. Implant telemetry circuit 744 may also function as a power receiver that receives power transmitted from an external device through an inductive couple. Electrode(s) 707 allow for delivery of the neurostimulation pulses in the monopolar mode. Examples of electrode(s) 707 include electrode 426 and electrode 418 in IPG 404 as illustrated in FIG. 4.

In one embodiment, implantable stimulator 704 is used as a master database. A patient implanted with implantable stimulator 704 (such as may be implemented as IPG 604) may therefore carry patient information needed for his or her medical care when such information is otherwise unavailable. Implant storage device 746 is configured to store such patient information. For example, the patient may be given a new RC 632 and/or travel to a new clinic where a new CP 630 is used to communicate with the device implanted in him or her. The new RC 632 and/or CP 630 can communicate with implantable stimulator 704 to retrieve the patient information stored in implant storage device 746 through implant telemetry circuit 744 and wireless communication link 640 and allow for any necessary adjustment of the operation of implantable stimulator 704 based on the retrieved patient information. In various embodiments, the patient information to be stored in implant storage device 746 may include, for example, positions of lead(s) 708 and electrodes 706 relative to the patient's anatomy (transformation for fusing computerized tomogram (CT) of post-operative lead placement to magnetic resonance imaging (MRI) of the brain), clinical effect map data, objective measurements using quantitative assessments of symptoms (for example using micro-electrode recording, accelerometers, and/or other sensors), and/or any other information considered important or useful for providing adequate care for the patient. In various embodiments, the patient information to be stored in implant storage device 746 may include data transmitted to implantable stimulator 704 for storage as part of the patient information and data acquired by implantable stimulator 704, such as by using sensing circuit 742.

In various embodiments, sensing circuit 742 (if included), stimulation output circuit 212, stimulation control circuit 714, implant telemetry circuit 744, implant storage device 746, and power source 748 are encapsulated in a hermetically sealed implantable housing or case, and electrode(s) 707 are formed or otherwise incorporated onto the case. In various embodiments, lead(s) 708 are implanted such that electrodes 706 are placed on and/or around one or more targets to which the neurostimulation pulses are to be delivered, while implantable stimulator 704 is subcutaneously implanted and connected to lead(s) 708 at the time of implantation.

Figure 8:
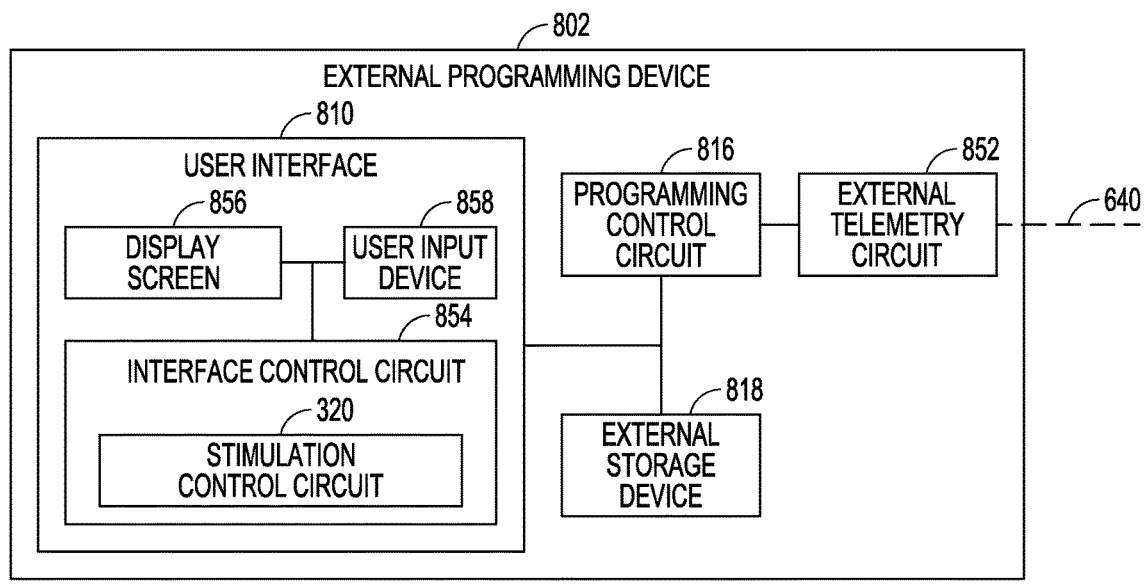
FIG. 8 illustrates an embodiment of an external programming device of an implantable neurostimulation system, such as the implantable neurostimulation system of FIG. 6.

FIG. 8 illustrates an embodiment of an external programming device 802 of an implantable neurostimulation system, such as system 600. External programming device 802 represents an example of programming device 102 or 302, and may be implemented, for example, as CP 630 and/or RC 632. External programming device 802 includes an external telemetry circuit 852, an external storage device 818, a programming control circuit 816, and a user interface 810.

External telemetry circuit 852 provides external programming device 802 with wireless communication with another device such as implantable stimulator 704 via wireless communication link 640, including transmitting the plurality of stimulation parameters to implantable stimulator 704 and receiving information including the patient data from implantable stimulator 704. In one embodiment, external telemetry circuit 852 also transmits power to implantable stimulator 704 through an inductive couple.

In various embodiments, wireless communication link 640 can include an inductive telemetry link (near-field telemetry link) and/or a far-field telemetry link (RF telemetry link). For example, because DBS is often indicated for movement disorders which are assessed through patient activities, gait, balance, etc., allowing patient mobility during programming and assessment is useful. Therefore, when system 600 is intended for applications including DBS, wireless communication link 640 includes at least a far-field telemetry link that allows for communications between external programming device 802 and implantable stimulator 704 over a relative long distance, such as up to about 20 meters. External telemetry circuit 852 and implant telemetry circuit 744 each include an antenna and RF circuitry configured to support such wireless telemetry.

External storage device 818 stores one or more stimulation waveforms for delivery during a neurostimulation therapy session, such as a DBS therapy session, as well as various parameters and building blocks for defining one or more waveforms. The one or more stimulation waveforms may each be associated with one or more stimulation fields and represent a pattern of neurostimulation pulses to be delivered to the one or more stimulation fields during the neurostimulation therapy session. In various embodiments, each of the one or more stimulation waveforms can be selected for modification by the user and/or for use in programming a stimulation device such as implantable stimulator 704 to deliver a therapy. In various embodiments, each waveform in the one or more stimulation waveforms is definable on a pulse-by-pulse basis, and external storage device 818 may include a pulse library that stores one or more individually definable pulse waveforms each defining a pulse type of one or more pulse types. External storage device 818 also stores one or more individually definable stimulation fields. Each waveform in the one or more stimulation waveforms is associated with at least one field of the one or more individually definable stimulation fields. Each field of the one or more individually definable stimulation fields is defined by a set of electrodes through a neurostimulation pulse is delivered. In various embodiments, each field of the one or more individually definable fields is defined by the set of electrodes through which the neurostimulation pulse is delivered and a current distribution of the neurostimulation pulse over the set of electrodes. In one embodiment, the current distribution is defined by assigning a fraction of an overall pulse amplitude to each electrode of the set of electrodes. Such definition of the current distribution may be referred to as "fractionalization" in this document. In another embodiment, the current distribution is defined by assigning an amplitude value to each electrode of the set of electrodes. For example, the set of electrodes may include 2 electrodes used as the anode and an electrode as the cathode for delivering a neurostimulation pulse having a pulse amplitude of 4 mA. The current distribution over the 2 electrodes used as the anode needs to be defined. In one embodiment, a percentage of the pulse amplitude is assigned to each of the 2 electrodes, such as 75% assigned to electrode 1 and 25% to electrode 2. In another embodiment, an amplitude value is assigned to each of the 2 electrodes, such as 3 mA assigned to electrode 1 and 1 mA to electrode 2. Control of the current in terms of percentages allows precise and consistent distribution of the current between electrodes even as the pulse amplitude is adjusted. It is suited for thinking about the problem as steering a stimulation locus, and stimulation changes on multiple contacts simultaneously to move the locus while holding the stimulation amount constant. Control and displaying the total current through each electrode in terms of absolute values (e.g. mA) allows precise dosing of current through each specific electrode. It is suited for changing the current one contact at a time (and allows the user to do so) to shape the stimulation like a piece of clay (pushing/pulling one spot at a time).

Programming control circuit 816 represents an example of programming control circuit 316 and generates the plurality of stimulation parameters, which is to be transmitted to implantable stimulator 704, based on a specified neurostimulation program (e.g., the pattern of neurostimulation pulses as represented by one or more stimulation waveforms and one or more stimulation fields, or at least certain aspects of the pattern). The neurostimulation program may be created and/or adjusted by the user using user interface 810 and stored in external storage device 818. In various embodiments, programming control circuit 816 can check values of the plurality of stimulation parameters against safety rules to limit these values within constraints of the safety rules. In one embodiment, the safety rules are heuristic rules.

User interface 810 represents an example of user interface 310 and allows the user to define the pattern of neurostimulation pulses and perform various other monitoring and programming tasks. User interface 810 includes a display screen 856, a user input device 858, and an interface control circuit 854. Display screen 856 may include any type of interactive or non-interactive screens, and user input device 858 may include any type of user input devices that supports the various functions discussed in this document, such as touchscreen, keyboard, keypad, touchpad, trackball, joystick, and mouse. In one embodiment, user interface 810 includes a GUI. The GUI may also allow the user to perform any functions discussed in this document where graphical presentation and/or editing are suitable as may be appreciated by those skilled in the art.

Interface control circuit 854 controls the operation of user interface 810 including responding to various inputs received by user input device 858 and defining the one or more stimulation waveforms. Interface control circuit 854 includes stimulation control circuit 320.

In various embodiments, external programming device 802 can have operation modes including a composition mode and a real-time programming mode. Under the composition mode (also known as the pulse pattern composition mode), user interface 810 is activated, while programming control circuit 816 is inactivated. Programming control circuit 816 does not dynamically updates values of the plurality of stimulation parameters in response to any change in the one or more stimulation waveforms. Under the real-time programming mode, both user interface 810 and programming control circuit 816 are activated. Programming control circuit 816 dynamically updates values of the plurality of stimulation parameters in response to changes in the set of one or more stimulation waveforms and transmits the plurality of stimulation parameters with the updated values to implantable stimulator 704.

Figure 9:
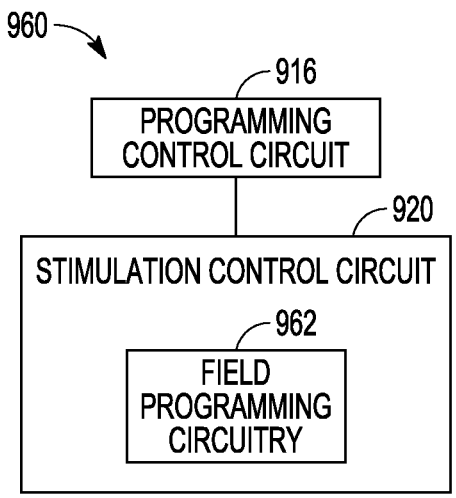
FIG. 9 illustrates an embodiment of a system for optimizing a stimulation field set.

FIG. 9 illustrates an embodiment of a system 960 for optimizing a stimulation field set according to a subtraction-based programming paradigm. System 960 can be implemented as part of a system for delivering neurostimulation to tissue of a patient using a stimulation device coupled to a plurality of electrodes and controlling the delivery of the neurostimulation by a user, such as neurostimulation system 100, 500, or 600. When system 960 is implemented in system 100, 500, or 600, the stimulation device can include stimulation device 104, stimulation device 204, IPG 404, implantable stimulator or IPG 504, IPG 604, or implantable stimulator 704, and the plurality of electrodes can include electrodes 106, 206, 406, 506, 606, and 706.

System 960 can include a programming control circuit 916 and a stimulation control circuit 920. Programming control circuit 916 can program the stimulation device for delivering the neurostimulation according to a stimulation program. The stimulation program specifies a present stimulation field set including one or more stimulation fields each defined by a set of active electrodes selected from the plurality of electrodes. Stimulation control circuit 920 can determine the stimulation program and include field programming circuitry 962. Field programming circuitry 962 can set the present stimulation field set to an initial stimulation field set. The initial stimulation field set specifies a plurality of stimulation fields and allows for the delivery of the neurostimulation to produce an intended effect in the patient. Field programming circuitry 962 can then identify an optimal stimulation field set that satisfies one or more optimization criteria by removing one or more stimulation fields from the initial stimulation field set.

In one embodiment, the one or more stimulation fields in each stimulation field set are each further defined by a distribution of energy of the neurostimulation over the active electrodes. The distribution of energy can be specified by specifying a percentage of current of the neurostimulation on each of the active electrodes (i.e., by fractionalization). An equivalent way for defining the one or more stimulation fields in each stimulation field set is to specify a distribution of energy of the neurostimulation over the plurality of electrodes (i.e., all the electrodes, with zero energy or zero percent of current specified for each inactive electrode).

In various embodiments, system 960 may be implemented as part of external programming device 802 (which may be implemented, for example, as CP 630 and/or RC 632) or implemented as any device allowing for determination of stimulation parameters, including any computer programmed for determining stimulation parameters. System 960 can include programming control circuit 816 and stimulation control circuit 920. Programming control circuit 916 can represent an example of programming control circuit 816 and can be configured to program a stimulation device, such as stimulation device 104 including but not limited to its various embodiments as discussed in this document, for delivering neurostimulation according to a pattern of neurostimulation pulses defined by one or more stimulation waveforms. Stimulation control circuit 920 can represent an example of stimulation control circuit 320 and can be configured to determine the neurostimulation program. An example of the neurostimulation program includes the stimulation program for controlling the delivery of the neurostimulation in performing a method of optimizing the stimulation field set according to the subtraction-based programming paradigm.

In various embodiments, the stimulation program defined by stimulation control circuit 920 can include a pattern of neurostimulation pulses. Programming control circuit 916 can generate a plurality of stimulation parameters according to the pattern of neurostimulation pulses. In embodiments in which programming control circuit 916 is part of a programming device such as external programming device 802, programming control circuit 916 can transmit the plurality of stimulation parameters to implantable stimulator 704 to be used by stimulation control circuit 714 to control delivery of neurostimulation from stimulation output circuit 212. In various embodiments, the pattern of neurostimulation pulses are defined by the one or more stimulation waveforms and one or more stimulation fields. Stimulation control circuit 320 can determine the one or more stimulation waveforms and the one or more stimulation fields. Each pulse in the pattern of neurostimulation pulses has a stimulation waveform being the waveform of the pulse and a stimulation field specifying electrodes through which the pulse is delivered. The one or more stimulation fields can each be defined by a set of active electrodes through which one or more neurostimulation pulses of the pattern of neurostimulation pulses are delivered to the patient. In various embodiments, each neurostimulation pulse has an overall current amplitude, and the one or more stimulation fields are each further defined by a fractionalization assigning a fraction of the overall current amplitude to each electrode of the set of active electrodes.

Figure 10:
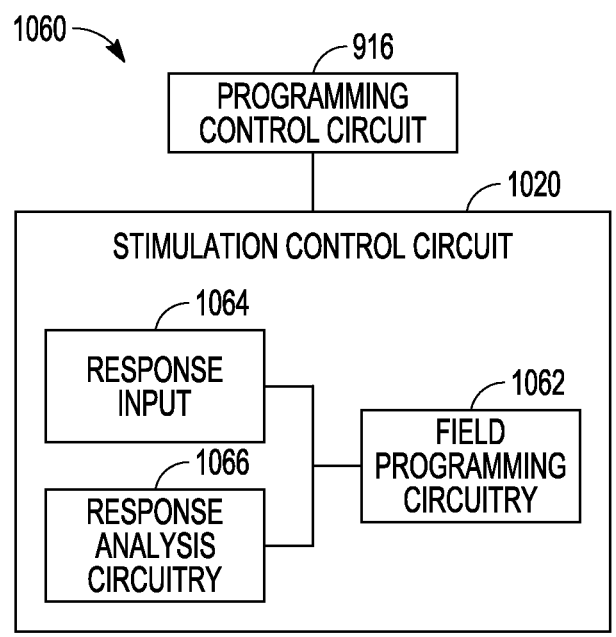
FIG. 10 illustrates another embodiment of a system for optimizing a stimulation field set.

FIG. 10 illustrates another embodiment of a system 1060 for optimizing a stimulation field set according to the subtraction-based programming paradigm. System 1060 represents an example of system 960 and can include programming control circuit 916 and a stimulation control circuit 1020.

Stimulation control circuit 1020 represents an example of stimulation control circuit 1020 and can include a response input 1064, response analysis circuitry 1066, and field programming circuitry 1062. Response input 1064 can receive a response signal indicative of effects of the neurostimulation. In one embodiment, response input 1064 can receive the response signal from a user input device such as user input device 858. The response signal can include a user input indicating the patient's perception of the delivery of the neurostimulation. In another embodiment, response input 1064 can receive the response signal from a sensing circuit, such as sensing circuit 742. The response signal can include a sensed biomarker signal indicative of effects of the delivery of the neurostimulation in the patient. This allows for the stimulation field set to be optimized automatically using a closed-loop system that can be implemented within the stimulation device such as implantable stimulator 704 or implemented with the programming device such as external programming device 802 receiving the sensed biomarker signal from the stimulation device or a separate sensing device.

Response analysis circuitry 1066 can analyze the response signal received by response input 1064 for intended and unintended effects of the neurostimulation and produce effects information based on the analysis. The effects information allows for determination of whether a stimulation field set is optimized based on one or more optimization criteria. In various embodiments, the one or more optimization criteria can include an intended effect threshold level for a measure of an intended effect and an unintended effect threshold level for a measure of an unintended effect. The measures for the intended and unintended effect can each include a patient perception and/or a parameter measured from a sensed biomarker signal. In this document, an "intended effect" (also referred to as a therapeutic effect or a stimulation target) includes a therapeutic or other desirable effect of the neurostimulation, and an "unintended effect" (also referred to as a side effect) includes an undesirable effect of the neurostimulation. In various embodiments, the one or more optimization criteria can include, for example, (i) maintaining an intended effect without causing an unintended effect, (ii) maintaining an intended effect above an acceptable level while minimizing an unintended effect, (iii) maximizing an intended effect while maintaining an unintended effect below an acceptable level, or (iv) maintaining an intended effect above an acceptable level and maintaining an unintended effect below an acceptable level. The unintended effect can be any unintended effect, any unacceptable unintended effect, or a specified type of unintended effect. In various embodiment, the one or more optimization criteria can further include minimizing an amount of the neurostimulation required for each of (i)-(iv). A stimulation field set can be considered to be "optimized" or declared to be an "optimal" stimulation field set when it satisfies the one or more optimization criteria or when it is the best of a group of stimulation field sets in view of the one or more optimization criteria.

Field programming circuitry 1062 represents an example of field programming circuitry 962 and can perform a method for determining the stimulation program for identifying an optimal stimulation field set for the patient. Field programming circuitry 1062 can perform the method by executing a subtraction-based programming algorithm to determine the optimal stimulation field set. The method, including its various embodiments, is discussed below as examples of a method or steps of the method with reference to FIGS. 11-19. In one embodiment, a storage device (e.g., external storage device 818 when system 1060 is implemented in external programming device 802) can include a non-transitory computer-readable storage medium including instructions, which when executed by a processor of stimulation control circuit 1020, cause the processor (or portion thereof) to perform the method (including any method or various steps of the method discussed in this document, for example with reference to FIGS. 11-19). In various embodiments, the method is performed for purposes of determining a stimulation program including parameters defining one or more stimulation field for delivering a neurostimulation therapy to the patient.

Figure 11:
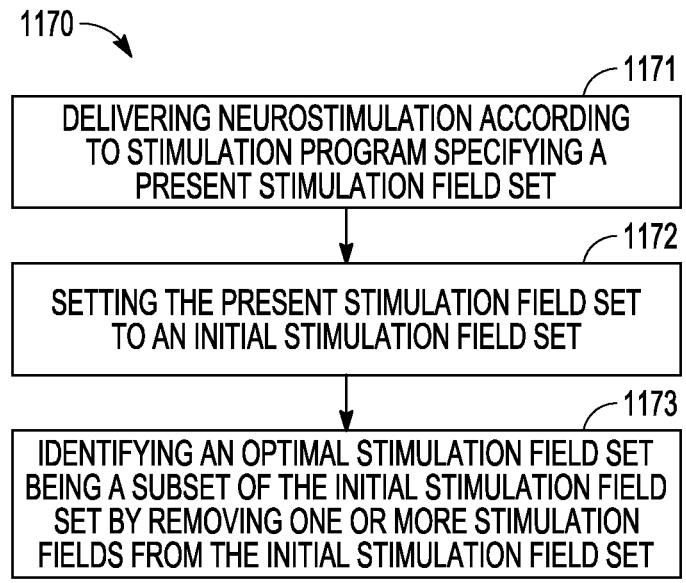
FIG. 11 illustrates an embodiment of a subtraction-based programming method for optimizing a stimulation field set.

FIG. 11 illustrates an embodiment of a subtraction-based programming method 1170 for optimizing a stimulation field set according to the subtraction-based programming paradigm. In one embodiment, method 1170 is performed using a neurostimulation system that includes system 960 or 1060. The neurostimulation system can deliver neurostimulation to tissue of a patient using a stimulation device coupled to a plurality of electrodes and controlling the delivery of the neurostimulation by a user.

At 1171, the neurostimulation is delivered according to a stimulation program. The stimulation program specifies a present stimulation field set including one or more stimulation fields each defined by a set of active electrodes selected from the plurality of electrodes. At 1172, the present stimulation field set is set to an initial stimulation field set specifying a plurality of stimulation fields. The initial stimulation field allows for the delivery of the neurostimulation to produce an intended effect in the patient. At 1173, an optimal stimulation field set that satisfies one or more optimization criteria is identified by removing one or more stimulation fields from the initial stimulation field set. The optimal stimulation field set includes one or more stimulation fields being a subset of the plurality of stimulation fields of the initial stimulation field set. In one embodiment, the one or more stimulation fields are each further defined by a distribution of energy of the neurostimulation over the active electrodes. After each setting (update) of the present stimulation field set, the stimulation device delivers the neurostimulation according to the stimulation program specifying the newly uprated present stimulation field set.

Figure 12:
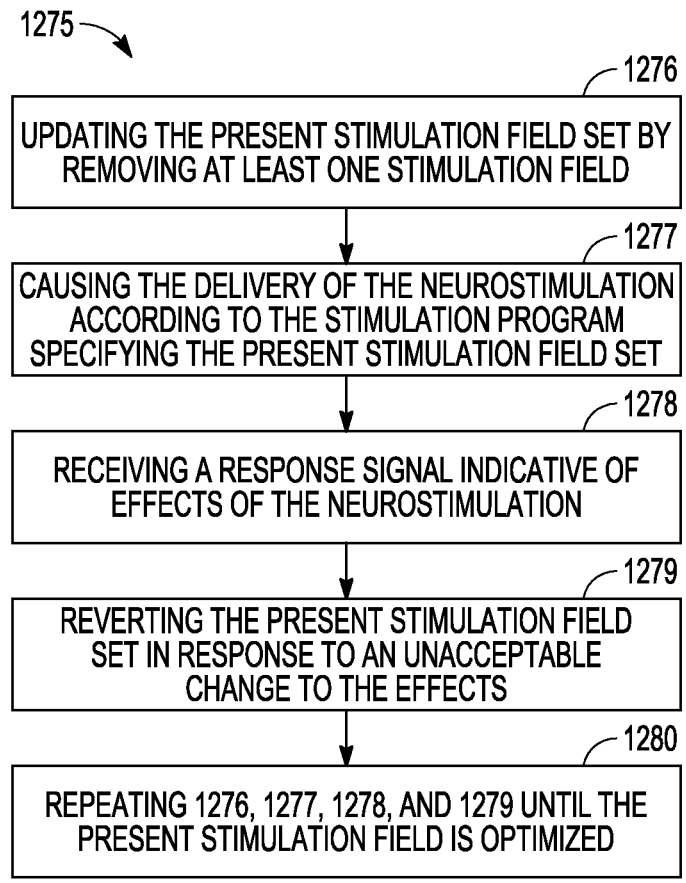
FIG. 12 illustrates an embodiment of a method for identifying an optimal stimulation field set, such as used in the method of FIG. 11.

FIG. 12 illustrates an embodiment of a method 1275 for identifying an optimal stimulation field set, such as used in method 1170 for performing step 1173. In one embodiment, method 1275 is also performed using the neurostimulation system that includes system 960 or 1060, as discussed for method 1170.

At 1276, at least one stimulation field is removed from the present stimulation field set to update the present stimulation field set. At 1277, the stimulation device is caused (by programming) to deliver the neurostimulation according to the stimulation program specifying the present stimulation field set. At 1278, a response signal is received. The response signal is indicative of effects of the neurostimulation delivered according to the stimulation program specifying the present stimulation field set. In various embodiments, the response signal can include a user input indicating the patient's perception of the delivery of the neurostimulation and/or a biomarker signal indicative of effects of the delivery of the neurostimulation in the patient. In various embodiments, the received response signal is analyzed for intended and unintended effects of the neurostimulation. Based on the analysis, effects information can be produced to allow for determination of whether the present stimulation field set is optimized based on one or more optimization criteria.

At 1279, the present stimulation field set is reverted to the pre-update present stimulation field set in response to the response signal indicating an unacceptable change to the effects indicated by the response signal. The unacceptable change can include a decrease in the intended effect and/or an increase in the unintended effect. After the reverting (i.e., removal of the present stimulation field, the latest field evaluated), the following may happen: (1) there is a reduction in the unintended effect, and (2) there is a reduction in the intended effect. As such, it is desirable to make a change that accomplishes (1) without (2) occurring.

In one embodiment, in response to the increase in the unintended effect, after the reverting, one or more blocking fields are added. The delivery of neurostimulation energy to the one or more blocking fields has a blocking effect in preventing the delivery of neurostimulation energy from causing an unintended effect or reducing that unintended effect. The blocking effect can be achieved, for example, by allowing for a "blocking pulse" to precede a stimulating pulse, for the purpose of preventing the stimulation at a portion of the present stimulation field (the portion responsible for the unintended effect). Thus, a "block field" refers to a field to which the blocking pulse is delivered. This blocking pulse would necessarily use a blocking field that only blocks part of the present stimulation field because it is not desirable to block the intended effect. The placement of such a blocking field may require a trial-and-error process, or multiple blocking fields may be set to cover the present stimulation field and one or more blocking fields are then removed by following the subtraction-based programming method as applied to optimizing a blocking field set.

In another embodiment, in response to the increase in the unintended effect, after the reverting, the present stimulation field set is modified for a field shape providing for at least one of use of an inherent blocking effect or use of hyperpolarizing lobes to prevent the delivery of neurostimulation energy from causing an unintended effect or reducing that unintended effect. The shape of the present stimulation field set can be changed in some way. For example, the present stimulation field set can be split into multiple smaller fields before the performance of method 1275 continues, or the present stimulation field can be adapted to block a portion of itself and then the performance of method 1275 continues with evaluating different placements of the blocking portion. Hyperpolarizing lobes refers to the lobes of the activating function. One technique for blocking is to adjust the present stimulation field set such that a portion where the activating function was depolarizing becomes hyperpolarizing. As an example, for fibers of passage where the activating function is a second difference of the voltage, addition of anodic current in the region to be blocked can be used to achieve the hyperpolarization. When current is to be conserved, cathodic current can be added to the case electrode, or perhaps to another part of the present stimulation field.

At 1280, steps 1276, 1277, 1278, and 1279 are repeated until the present stimulation field set is determined to be the optimal stimulation field set according to the one or more optimization criteria. In various embodiments, the optimal stimulation field set is identified from a list of stimulation field sets. The list can rotate through all possible stimulation fields provided for by the plurality of electrodes. The initial stimulation field set can specify many stimulation fields each defined by one or more electrodes selected from the plurality of electrodes. In one embodiment, performance of method 1275 stops in response to identification of any stimulation field set that satisfies the one or more optimization criteria (i.e., the list of stimulation field sets can include multiple optimal stimulation field sets, and identification of one of them is sufficient). In another embodiment, performance of method 1275 stops in response to all the stimulation field sets on the list being evaluated (i.e., the list of stimulation field sets includes one optimal stimulation field set).

Figure 13E:
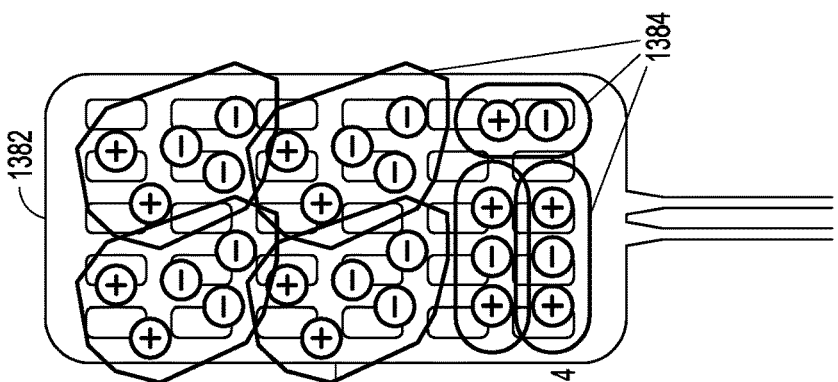
FIGS. 13A-E each illustrate an embodiment of a paddle electrode to be surgically implanted for delivering neurostimulation, with FIGS. 13B-E each illustrating an example of a stimulation field set.
Figure 13D:
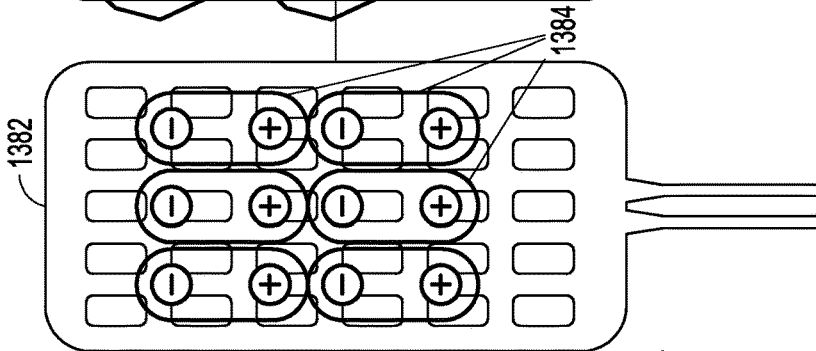
Figure 13C:
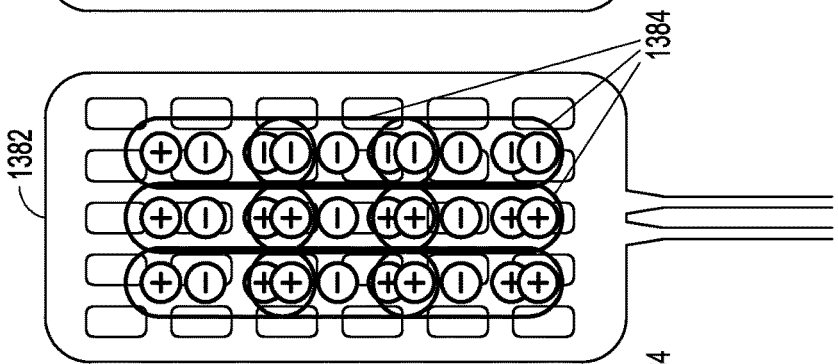
Figure 13B:
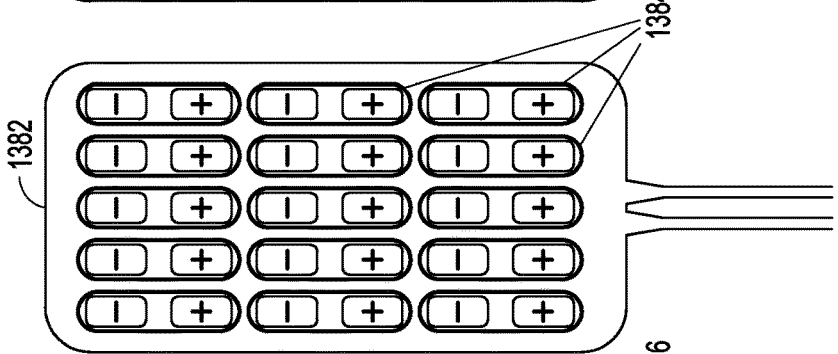
Figure 13A:
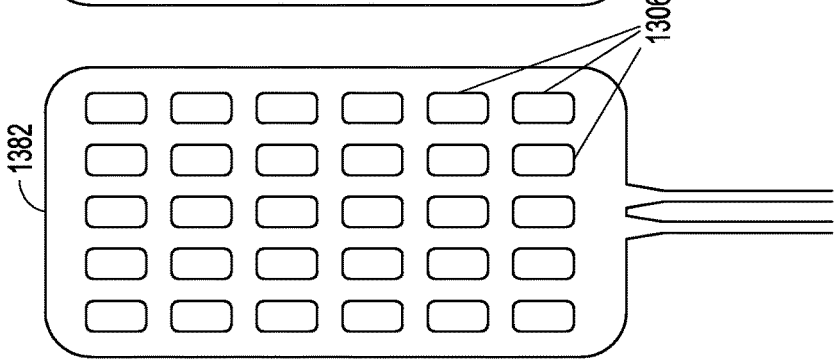

FIGS. 13A-E each illustrate an embodiment of a paddle electrode 1382 to be surgically implanted for delivering neurostimulation, with FIGS. 13B-E each illustrating an example of a stimulation field set. FIG. 13A shows paddle electrode 1382 with an electrode array including 30 electrodes (also referred to as contacts) 1306. FIG. 13B shows an example of a stimulation field set with 15 bipolar stimulation fields 1384. The illustrated stimulation field set can be stimulated sequentially. If the stimulation results in the coverage desired (even as part of a super set), then a placement of paddle electrode 1382 in the patient can be considered appropriate, and fine tuning can be post-operationally performed according to the subtraction-based programming paradigm. FIG. 13C shows another example of a stimulation field set including 9 tripolar fields 1384, with target poles or another arbitrary field assignment used. The stimulation fields can overlap. The center of the array can be preferentially evaluated. FIG. 13D shows another example of a stimulation field set including 6 bipolar fields 1384. FIG. 13E shows another example of a stimulation field set including 7 stimulation fields 1384 with different shapes. These shapes can be based on physical electrodes, target poles, and/or other field paradigm converted to physical electrodes.

FIGS. 14A-E each illustrate an embodiment of an electrode array at distal end of a lead 1408 to be percutaneously implanted for delivering neurostimulation, with FIGS. 14B-E each illustrating an example of a stimulation field set. FIG. 14B shows an example of a stimulation field set with 6 bipolar stimulation fields 1484 using electrodes 1406 on lead 1408. FIG. 14C shows an example of a stimulation field set with 9 tripolar stimulation fields 1484 using electrodes 1406 on leads 1408A-B. FIG. 14D shows an example of a stimulation field set with 5 bipolar stimulation fields 1484 using electrodes 1406 on leads 1408A-B. FIG. 14E shows an example of a stimulation field set with 4 multipolar stimulation fields 1484 using electrodes 1406 on leads 1408A-B.

In various embodiments, the examples of stimulation field sets as illustrated in FIGS. 13 and 14 can be used for optimizing a stimulation field set according to the subtraction-based programming paradigm. If delivery of the neurostimulation to a stimulation field set results in the coverage desired (even as part of a super set), then the placement of paddle electrode 1382 or lead 1408 can be considered appropriate for the patient, and fine tuning can be done later to substantially expedite an implantation process in the operation room. The subtraction-based programming paradigm provides for a method for the post-operational fine tuning.

Figure 15:
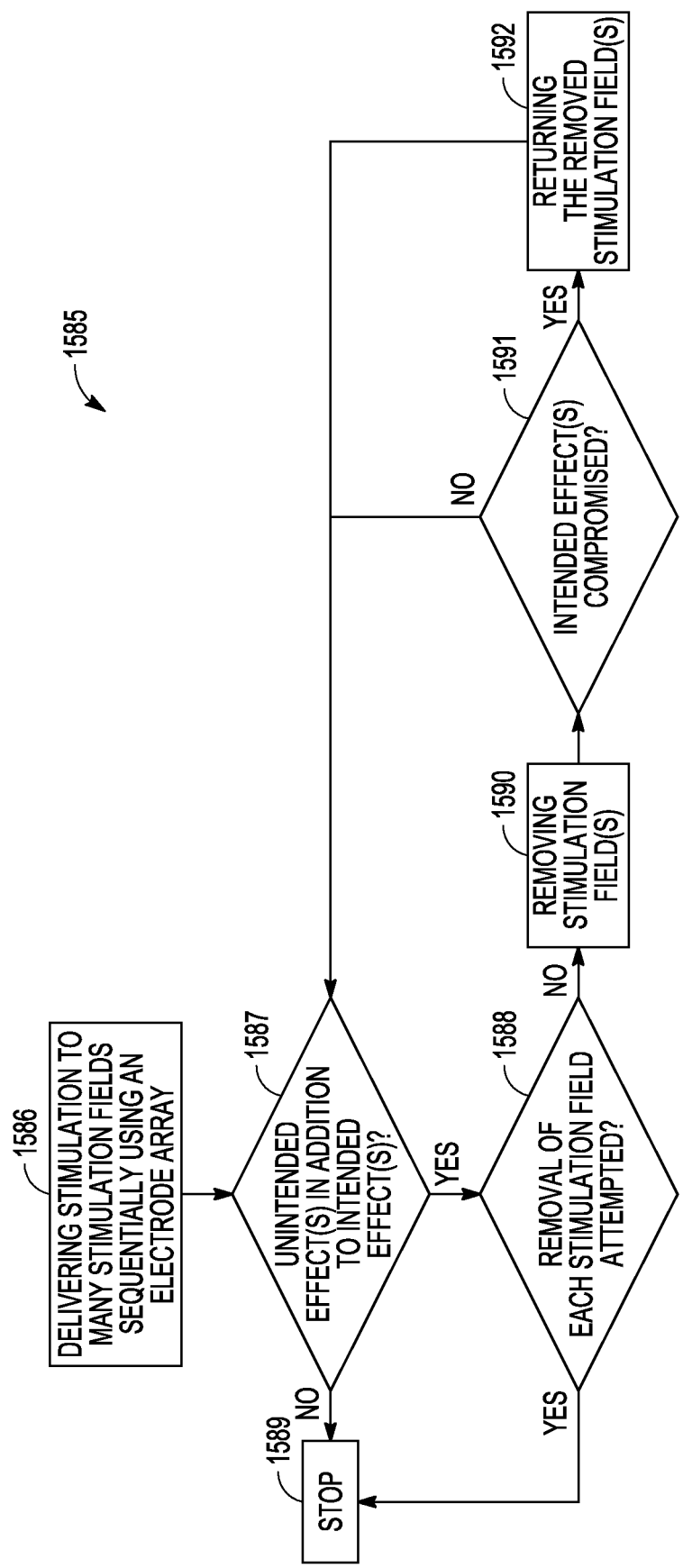
FIG. 15 illustrates an embodiment of a subtraction-based programming method as an application of the methods of FIGS. 11 and 12.

FIG. 15 illustrates an embodiment of a subtraction-based programming method 1585 as an application of methods 1170 and 1275. At 1586, neurostimulation is delivered to many stimulation fields using an electrode array, with the goal of stimulating target tissue to result in intended effect(s) and the likelihood of stimulating non-target tissue to result in unintended effect(s). At 1587, effects of the neurostimulation is evaluated. If the effects includes the intended effect(s) but not unintended effect(s), the performance of method 1585 stops at 1589. If the effects includes the intended effect(s) and unintended effect(s), and removal of each stimulation field from the many stimulation fields has been attempted, the performance of method 1585 also stops at 1589. If the effects includes the intended effect(s) and unintended effect(s), but removal of one or more stimulation fields from the many stimulation fields have not been attempted, one or more stimulation fields are removed at 1590. At 1591, whether the intended effect(s) are compromised is determined. If the intended effect(s) are not compromised, the performance of method 1585 processes back to 1587 for another iteration. If the intended effect(s) are compromised, the one or more stimulation field removed at 1590 are returned to the set of stimulation fields prior to the performance of step 1590, and then the performance of method 1585 processes back to 1587 for another iteration.

In other words, according to method 1585, following stimulation of many stimulation fields, stimulation fields are removed and response to the stimulation is evaluated. The removal of additional stimulation fields can stop once any stimulation field to which the stimulation results in unintended effect(s) has been removed, or when removal of all stimulation fields has been attempted (such that no more removal is possible without compromising the intended effect(s). In various embodiments, "many" stimulation fields can include at least 2 stimulation fields or at least 4 stimulation fields. Stimulation of the many stimulation fields can be delivered sequentially, one field at a time, using an electrode array such as one of those illustrated in FIGS. 13 and 14.

Figure 16:
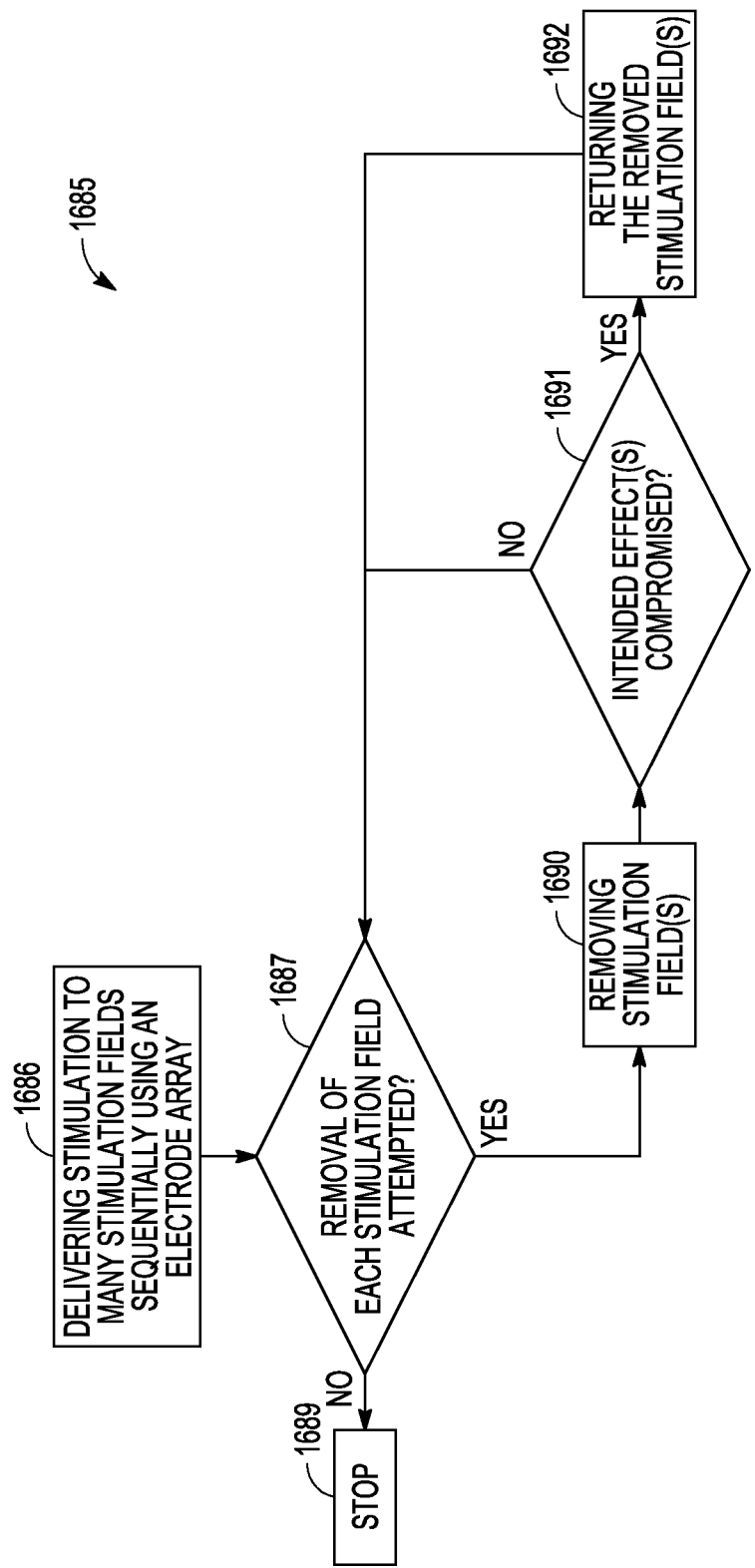
FIG. 16 illustrates another embodiment of a subtraction-based programming method as an application of the methods of FIGS. 11 and 12.

FIG. 16 illustrates another embodiment of a subtraction-based programming method 1685 as an application of methods 1170 and 1275. At 1686, neurostimulation is delivered to many stimulation fields using an electrode array, with the goal of stimulating target tissue to result in intended effect(s) and reduce the likelihood of stimulating non-target tissue to result in unintended effect(s). If removal of each stimulation field from the many stimulation fields has been attempted, the performance of method 1685 also stops at 1689. If removal of one or more stimulation fields from the many stimulation fields have not been attempted, one or more stimulation fields are removed at 1690. At 1691, whether the intended effect(s) are compromised is determined. If the intended effect(s) are not compromised, the performance of method 1685 processes back to 1688 for another iteration. If the intended effect(s) are compromised, the one or more stimulation field removed at 1690 are returned to the set of stimulation fields prior to the performance of step 1690, and then the performance of method 1685 processes back to 1688 for another iteration.

In other words, method 1685 is the same as method 1585 except for the purpose of maximizing energy efficiency, removal of all the stimulation fields is attempted even after an adequate number of stimulation fields has been removed to eliminate the unintended effect(s).

Various methods can be used to determine an order of removal of the stimulation field from the initial stimulation set (including "many" stimulation fields). One example includes using a simplex or simplex-like search method that is initialized with a polygon that includes all the stimulation field of the initial stimulation field set, and iteratively changes the shape of the polygon and reduces the area of the polygon. Another example includes initiating multiple simplices with different starting conditions to account for the possibility of multiple local minima. Additional examples can include golden-section or Fibonacci-based search methods. In various embodiments, non-linear search methods with one or more initial conditions can be used. In various embodiments, non-linear biologically inspired methods that account for multiple optima or regions of interest (ROIs) can be used, such as genetic algorithms, swarm algorithms, etc.

FIG. 17A-F each illustrate an embodiment of part of method 1585 or 1685 showing a step in performing the method using paddle electrode 1382 including an array of electrodes 1306. FIG. 17A-F also show stimulation fields 1784, a target region 1794 to which the delivery of the neurostimulation results in the intended effect(s), and side-effect regions 1796 to which the delivery of the neurostimulation results in the unintended effect(s). The optimal stimulation field set should include one or more stimulation fields that covers target region 1794 without covering side-effect regions 1796.

FIG. 17A shows many stimulation fields 1784 cover both target region 1784 and side-effect region 1796. For the operational room setting, placement of paddle electrode 1382 is adequate because target region 1794 can be stimulated. FIG. 17B shows removal of some of stimulation fields 1784 that results in less coverage of side-effect region 1796, while target region 1784 is still covered. FIG. 17C shows further removal of some of stimulation fields 1784 that results in further reduced coverage of side-effect region 1796, while target region 1784 is still covered. FIG. 17D shows further removal of some of stimulation fields 1784 that results in reduced coverage of target region 1784. FIG. 17E shows returning of the removed stimulation fields 1784 to restore the set of stimulation fields 1784 of FIG. 17C, thereby restoring coverage of target region 1784. FIG. 17F shows removal of additional stimulation fields 1784 that eliminates coverage of side-effect region 1796, while target region 1784 is still covered. Thus, the stimulation field set is optimized because it covers target region 1794 without covering side-effect regions 1796, as illustrated in FIG. 17F.

FIG. 18A-E each illustrate an embodiment of part of method 1585 or 1685 showing a step in performing the method using paddle electrode 1382 including an array of electrodes 1306. FIG. 18A-E also show stimulation fields 1784, target regions 1894, and side-effect regions 1896. FIG. 18A-E show an example where target and side-effect regions are juxtaposed, and addition of "blocking" (in addition to or in place of removing) is used to reduce the unintended effect(s). Thus, FIG. 18A-E further show blocking fields 1898 to which the delivery of the neurostimulation has a blocking effect in preventing the delivery of the neurostimulation from causing unintended effect(s). In some embodiments, blocking fields 1898 are smaller than stimulation fields 1784 to provide for higher resolution blocking.

FIG. 18A shows many stimulation fields 1784 cover both target region 1884 and side-effect region 1896. For the operational room setting, placement of paddle electrode 1382 is adequate because target region 1794 can be stimulated. FIG. 18B shows removal of some of stimulation fields 1784 that results in nearly no coverage of side-effect region 1796, while target region 1784 is not adequately covered. FIG. 18C shows restoration of a stimulation fields 1784 that results in increased coverage of side-effect region 1796, while target region 1784 is adequately covered. FIG. 18D shows addition of blocking fields 1898 to block the unintended effect(s) resulting from the stimulation field added as shown in FIG. 18C. The blocking effect can be achieved, for example, using pre-pulses or conditioning pulses. Examples of blocking are discussed in U.S. Pat. Nos. 7,742,810; 8,311,644; 8,788,059; and 9,375,575, all of which are assigned to Boston Scientific Neuromodulation Corporation and incorporated herein by reference in their entireties. FIG. 18E shows a solution to the unintended effect(s) being an alternative to that illustrated in FIG. 18D. Stimulation fields 1784 are modified in a manner that results in blocking or not stimulating being inherent in the field shape or the use of hyperpolarizing lobes.

In various embodiments, the system for performing the subtraction-based programming method, such as a neurostimulation system in which system 960 or 1060 is implemented, may be required to change stimulation fields (including removing stimulation fields) within a short period of time. In one embodiment, it is desirable to rotate through all of the stimulation fields within 25 ms (40 Hz). For example, 50 stimulation fields running at 40 Hz each results in an aggregate frequency of 2,000 Hz (i.e., the period of time T=500 µs). Therefore, charge of stimulation fields must be injected and properly recovered within 500 µs, assuming all the stimulation fields use the same pulse duration (PD, including charge injection and recovery phases). However, it is not required that all the stimulation fields use the same PD.

If different PDs are used, the sum of PD1 through PD50 should be less than or equal to 25 ms, assuming that all the stimulation fields run at the same frequency. However, the stimulation fields can run at different frequencies and even irregular patterns, and additional flexibility can be built into the system. In another embodiment, it is desirable to rotate through all of the stimulation fields within 50 ms (20 Hz). For example, 50 stimulation fields running at 20 Hz each result in an aggregate frequency of 1,000 Hz (i.e., the period of time T=1,000 μs). Therefore, charge of stimulation fields must be injected and properly recovered within 1,000 μs, assuming all the stimulation fields use the same PD. However, it is not required that all the stimulation fields use the same PD. If different PDs are used, the sum of PD1 through PD50 should be less than or equal to 50 ms, assuming that all the stimulation fields run at the same frequency. However, the stimulation fields can run at different frequencies and even irregular patterns, and additional flexibility can be built into the system.

In one embodiment, multiple stimulation fields that are an adequate distance apart from each other (such that interaction is sufficiently small) can be run at the same instant to preserve bandwidth. Examples of adequate distances apart can reasonably include 8 mm or more, 10 mm or more, or 12 mm or more.

FIG. 19 illustrates an embodiment of tools for editing a stimulation field set using a GUI, such as user interface 310 or 810. In one embodiment, the table of illustrated tools and optionally their descriptions can be displayed for the user on the GUI when needed. In various embodiments, the GUI can support manual removal, for example, with an eraser tool. The tools can enable manual removal of one or more stimulation fields in a predetermined or random sequence, with support to quickly undo and skip removal of a stimulation field that has been determined to be important to provide for the intended effect(s). In one embodiment, the GUI can automatically undo and skip removal of a stimulation field when such a need is determined.

In various embodiments, the subtraction-based programming paradigm can include automated or semi-automated processes (e.g., an automated or semi-automated binary search or another optimization routine for determining an order of removal of stimulation field(s). One embodiment can include use of heuristic search rules. Genetic or other algorithms that support multiple non-contiguous foci can also be found desirable and used.

It is to be understood that the above detailed description is intended to be illustrative, and not restrictive. Other embodiments will be apparent to those of skill in the art upon reading and understanding the above description. The scope of the invention should, therefore, be determined with reference to the appended claims, along with the full scope of equivalents to which such claims are entitled.

What is claimed is:

1. A method for delivering neurostimulation to tissue of a patient using a stimulation device coupled to a plurality of electrodes, the method comprising:
   delivering the neurostimulation using an initial stimulation field set to produce an intended effect in the patient, the initial stimulation field set including a plurality of stimulation fields each defined by a set of active electrodes selected from the plurality of electrodes;
   identifying one or more unnecessary stimulation fields in the initial stimulation field set, the one or more unnecessary stimulation fields being unnecessary for the delivery of the neurostimulation to maintain the intended effect, and
   delivering the neurostimulation using a stimulation field subset resulting from removing the identified one or more unnecessary stimulation fields from the initial stimulation field set.

2. The method of claim 1, further comprising:
   determining whether the stimulation field subset is optimized using one or more optimization criteria; and
   repeating the identifying one or more unnecessary stimulation fields and the delivering the neurostimulation using the stimulation field subset until the stimulation field subset is determined to be optimized.

3. The method of claim 2, wherein determining whether the stimulation field subset is optimized comprises determining whether the stimulation field subset best satisfies the one or more optimization criteria in a group of stimulation field subsets.

4. The method of claim 2, wherein determining whether the stimulation field subset is optimized comprises:
   receiving a response signal indicative of effects of the delivered neurostimulation; and
   determining whether the stimulation field subset is optimized by analyzing the response signal.

5. The method of claim 4, wherein receiving the response signal comprises receiving a user input indicative of the patient's perception of the delivery of the neurostimulation.

6. The method of claim 4, wherein identifying the one or more unnecessary stimulation fields in the initial stimulation filed comprises:
   setting a present stimulation field set to the initial stimulation field set;
   updating the present stimulation field set by removing at least one stimulation field from the present stimulation field set;
   delivering the neurostimulation using the updated present stimulation field set;
   analyzing the response signal to produce effects information indicative of effects of the neurostimulation delivered using the updated present stimulation field set;
   reverting the present stimulation field set to the pre-updating present stimulation field set in response to the effects information indicating one or more unacceptable effects; and
   repeating the updating, delivering, analyzing, and reverting until the present stimulation field set is determined to be optimized.

7. The method of claim 6, wherein reverting the present stimulation field set to the pre-updating present stimulation field set comprises reverting the present stimulation field set to the pre-updating present stimulation field set in response to the effect information indicating at least one of a decrease in the intended effect or an increase in an unintended effect.

8. The method of claim 6, further comprising declaring the present stimulation field set to be optimized in response to the effects information indicating that the intended effect is maintained without causing an unintended effect.

9. The method of claim 8, further comprising declaring the present stimulation field set to be optimized in response to the effects information indicating that an energy of the delivered neurostimulation is minimized while the intended effect is maintained without causing an unintended effect.

10. The method of claim 6, further comprising declaring the present stimulation field set to be optimized in response to the effects information indicating that the intended effect is maintained while one or more unintended effects are minimized.

11. The method of claim 10, further comprising declaring the present stimulation field set to be optimized in response to the effects information indicating that an energy of the delivered neurostimulation is minimized while the intended effect is maintained and the one or more unintended effects are minimized.

12. The method of claim 6, further comprising identifying the stimulation field subset from a plurality of test stimulation field sets, and the repeating comprises repeating the updating, delivering, analyzing, and reverting until each test stimulation field set of the plurality of test stimulation field sets has been used to result in the effects information allowing for the stimulation field subset to identified from the plurality of test stimulation field sets for best satisfying the one or more optimization criteria.

13. A system for delivering neurostimulation to tissue of a patient using a stimulation device coupled to a plurality of electrodes, the system comprising:
  a programming control circuit configured to program the stimulation device for delivering the neurostimulation using a present stimulation field set; and
  a stimulation control circuit configured to:
    set the present stimulation field set to an initial stimulation field set to produce an intended effect in the patient, the initial stimulation field set including a plurality of stimulation fields each defined by a set of active electrodes selected from the plurality of electrodes;
    identify one or more unnecessary stimulation fields in the initial stimulation field set, the one or more unnecessary stimulation fields being unnecessary for the delivery of the neurostimulation to maintain the intended effect, and
    set the present stimulation field set to a stimulation field subset resulting from removing the identified one or more unnecessary stimulation fields from the initial stimulation field set.

14. The system of claim 13, further including a user input device configured to receive a user input indicative of the patient's perception of the delivery of the neurostimulation, and wherein the stimulation control circuit is further configured to:
  receive a response signal indicative of effects of the neurostimulation, the response signal including the received user input; and
  analyze the received response signal and produce effects information allowing for the determination of whether the stimulation field subset is optimized according to one or more optimization criteria.

15. The system of claim 14, wherein the stimulation control circuit is configured to declare the stimulation field subset to be optimized in response to the effects information indicating that the intended effect is maintained without causing an unintended effect.

16. The system of claim 14, wherein the stimulation control circuit is configured to declare the stimulation field subset to be optimized in response to the effects information indicating that the intended effect is maintained while one or more unintended effects are minimized.

17. The system of claim 13, wherein the stimulation control circuit is further configured to determine the stimulation field subset by:
  updating the present stimulation field set by removing at least one stimulation field from the present stimulation field set;
  receiving a response signal indicative of effects of the neurostimulation delivered using the updated present stimulation field set;
  producing effects information by analyzing the received response signal;
  reverting the present stimulation field set to the pre-updating present stimulation field set in response to the effects information indicating one or more unacceptable effects; and
  repeating the updating, delivering, receiving, producing, and reverting until the present stimulation field set is determined to be optimized, wherein the optimized present stimulation field set is the stimulation field subset.

18. The system of claim 17, wherein the stimulation control circuit is configured to identify the stimulation field subset from a list of test stimulation field subsets, and the repeating comprises repeating the updating, delivering, receiving, producing, and reverting until each test stimulation field subset of the list of test stimulation field subsets has been used as the present stimulation field set to result in the effects information allowing for the stimulation field subset to identified from the list of test stimulation field subsets for best satisfying one or more optimization criteria.

19. A non-transitory computer-readable storage medium including instructions, which when executed by a machine, cause the machine to perform a method for delivering neurostimulation to tissue of a patient using a stimulation device coupled to a plurality of electrodes, the method comprising:
  delivering the neurostimulation using an initial stimulation field set to produce an intended effect in the patient, the initial stimulation field set including a plurality of stimulation fields each defined by a set of active electrodes selected from the plurality of electrodes;
  identifying one or more unnecessary stimulation fields in the initial stimulation field set, the one or more unnecessary stimulation fields being unnecessary for the delivery of the neurostimulation to maintain the intended effect, and
  delivering the neurostimulation using a stimulation field subset resulting from removing the identified one or more unnecessary stimulation fields from the initial stimulation field set.

20. The non-transitory computer-readable storage medium of claim 19, wherein identifying the one or more unnecessary electrodes in the initial set of active electrodes comprises:
  setting a present stimulation field set to the initial stimulation field set;
  updating the present stimulation field set by removing at least one stimulation field from the present stimulation field set;
  delivering the neurostimulation using the updated present stimulation field set;
  receiving a response signal indicative of effects of the neurostimulation delivered using the updated present stimulation field set;
  analyzing the received response signal to produce effects information;

reverting the present stimulation field set to the pre-updating present stimulation field set in response to the effects information indicating one or more unacceptable effects; and repeating the updating, delivering, receiving, analyzing, and reverting until the present stimulation field set is determined to be optimized.

\* \* \* \* \*